(12) United States Patent
Kiranyaz et al.

(10) Patent No.: US 12,033,071 B2
(45) Date of Patent: Jul. 9, 2024

(54) GENERALIZED OPERATIONAL PERCEPTRONS: NEW GENERATION ARTIFICIAL NEURAL NETWORKS

(71) Applicant: QATAR UNIVERSITY, Doha (QA)

(72) Inventors: Serkan Kiranyaz, Doha (QA); Turker Ince, Izmir (TR); Moncef Gabbouj, Tampere (FI); Alexandros Iosifidis, Tampere (FI)

(73) Assignee: QATAR UNIVERSITY, Doha (QA)

( * ) Notice: Subject to any disclaimer, the term of this patent is extended or adjusted under 35 U.S.C. 154(b) by 1245 days.

(21) Appl. No.: 16/968,789

(22) PCT Filed: Feb. 7, 2017

(86) PCT No.: PCT/IB2017/050658
§ 371 (c)(1),
(2) Date: Aug. 10, 2020

(87) PCT Pub. No.: WO2018/146514
PCT Pub. Date: Aug. 16, 2018

(65) Prior Publication Data
US 2021/0097389 A1    Apr. 1, 2021

(51) Int. Cl.
*G06N 3/08*    (2023.01)
*G06N 3/04*    (2023.01)

(52) U.S. Cl.
CPC ............... *G06N 3/08* (2013.01); *G06N 3/04* (2013.01)

(58) Field of Classification Search
CPC .................................. G06N 3/04; G06N 3/08
(Continued)

(56) References Cited

U.S. PATENT DOCUMENTS

2003/0190603 A1* 10/2003 Larder .................. G16B 20/20
                                                                435/5
2003/0191728 A1    10/2003 Kulkarni et al.
(Continued)

FOREIGN PATENT DOCUMENTS

| CN | 101799888 A   | 8/2010 |
| CN | 104050505 A   | 9/2014 |
| EP | 3 026 600 A2  | 6/2016 |

OTHER PUBLICATIONS

International Preliminary Report on Patentability issued in corresponding International Application No. PCT/IB2017/050658 on May 19, 2017.
(Continued)

*Primary Examiner* — Tsu-Chang Lee
(74) *Attorney, Agent, or Firm* — SQUIRE PATTON BOGGS (US) LLP

(57) ABSTRACT

Certain embodiments may generally relate to various techniques for machine learning. Feed-forward, fully-connected Artificial Neural Networks (ANNs), or the so-called Multi-Layer Perceptrons (MLPs) are well-known universal approximators. However, their learning performance may vary significantly depending on the function or the solution space that they attempt to approximate for learning. This is because they are based on a loose and crude model of the biological neurons promising only a linear transformation followed by a nonlinear activation function. Therefore, while they learn very well those problems with a monotonous, relatively simple and linearly separable solution space, they may entirely fail to do so when the solution space is highly nonlinear and complex. In order to address this drawback and also to accomplish a more generalized model of biological neurons and learning systems, Generalized
(Continued)

Operational Perceptrons (GOPs) may be formed and they may encapsulate many linear and nonlinear operators.

15 Claims, 11 Drawing Sheets

(58) Field of Classification Search
 USPC .......................................................... 706/25
 See application file for complete search history.

(56) References Cited

U.S. PATENT DOCUMENTS

| | | | |
|---|---|---|---|
| 2011/0218796 A1 | 9/2011 | Suzuki et al. | |
| 2011/0225112 A1* | 9/2011 | Cameron | G16Z 99/00 706/15 |
| 2012/0057779 A1* | 3/2012 | El Dokor | G06F 18/24133 382/154 |
| 2012/0303562 A1 | 11/2012 | Paguio | |
| 2015/0242747 A1* | 8/2015 | Packes | G06N 3/045 706/17 |
| 2016/0072590 A1 | 3/2016 | Tu et al. | |
| 2017/0175169 A1* | 6/2017 | Lee | G01N 33/54373 |

OTHER PUBLICATIONS

International Search Report and Written Opinion issued in corresponding International Application No. PCT/IB2017/050658 on May 19, 2017.
Okan Kopuklu et al., "Convolutional Neural Networks with Layer Reuse", Technical University of Munich Institute for Human-Machine Communication, 5 pages, Feb. 2019, https://github.com/okankop/CNN-layer-reuse.
Chinese Office Action issued in corresponding Chinese Patent Application No. 201780085807.1 on Dec. 29, 2023.
Serkan Kiranyaz et al., "Generalized Model of Biological Neural Networks: Progressive Operational Perceptrons", 2017 International Joint Conference on Neural Networks (IJCNN), May 19, 2017, 9 pages.

* cited by examiner

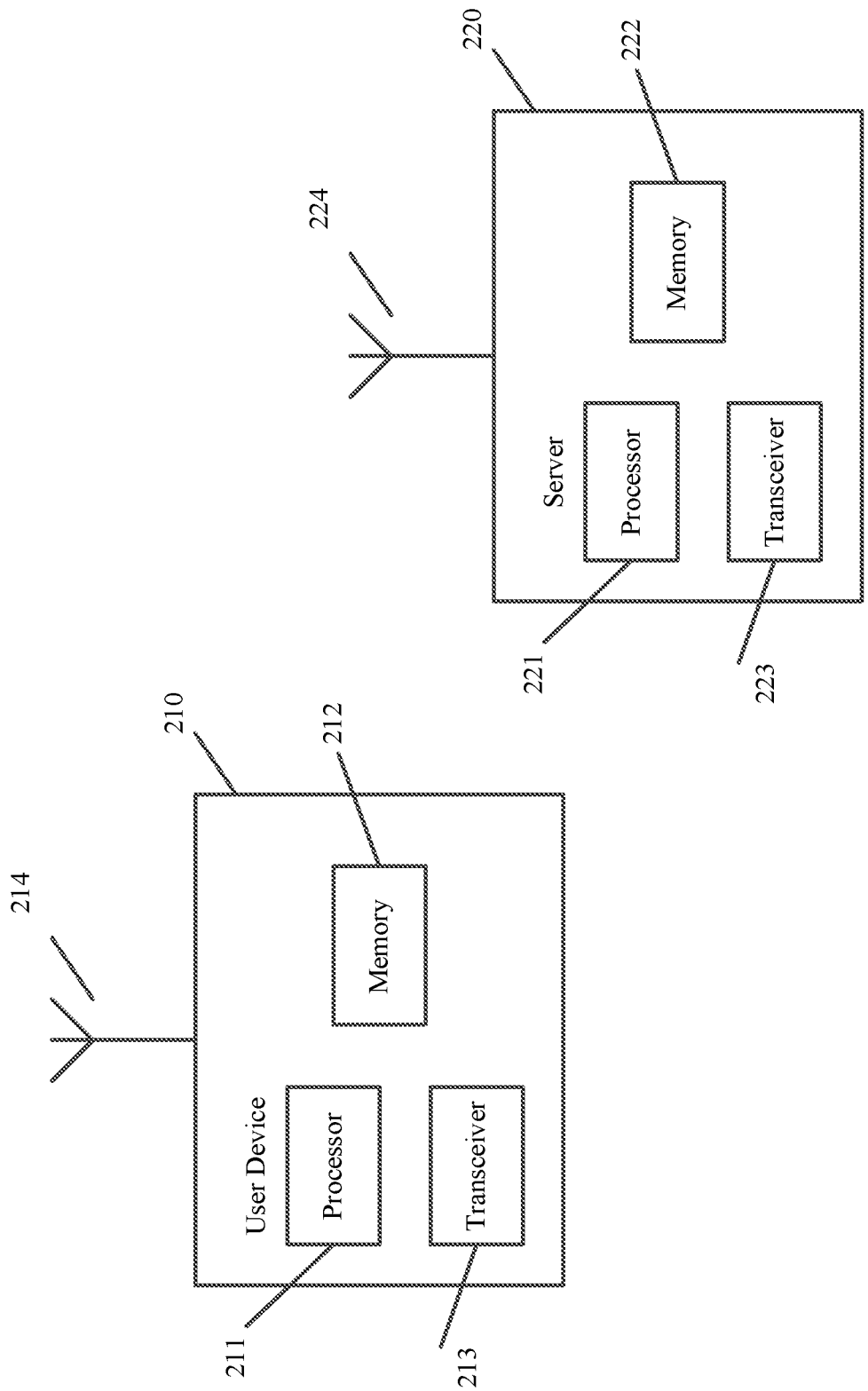

GENERALIZED OPERATIONAL PERCEPTRONS: NEW GENERATION ARTIFICIAL NEURAL NETWORKS

CROSS REFERENCE TO RELATED APPLICATION

This application is related to and claims the priority from PCT International Application No. PCT/IB2017/050658, filed on Feb. 7, 2017. The disclosure of the prior application is hereby incorporated by reference in its entirety.

FIELD OF THE INVENTION

Certain embodiments may generally relate to various techniques for machine learning. More specifically, certain embodiments of the present invention generally relate to feed forward, fully-connected Artificial Neural Networks (ANNs), training Generalized Operational Perceptrons (GOPs), and achieving self-organized and depth-adaptive GOPs with Progressive Operational Perceptrons (POPs).

BACKGROUND OF THE INVENTION

Learning in the broader sense can be in the form of classification, data regression, feature extraction and syntheses, or function approximation. For instance the objective for classification is finding out the right transformation of the input data (raw signal, data or feature vector) of each class to a distinct location in N-dimensional space that is far and well-separated from the others where N is the number of classes. Therefore, a challenge in learning is to find the right transformation (linear or non-linear) or in general, the right set of consecutive transformations so as to accomplish the underlying learning objective. For this purpose most existing classifiers use only one or few (non-)linear operators. One example is Support Vector Machines (SVMs) where one has to make the critical choice of the (non-)linear kernel function that will be used and subsequently define appropriate parameters. Even if one can optimize the performance of the classifier with respect to the kernel function's parameters, choosing an inappropriate kernel function can lead to far inferior performance, when compared to the performance that can be achieved by using the kernel function fitting to the characteristics of the problem at hand.

Consider for instance, two sample feature transformations (FS-1 and FS-2) illustrated in FIG. 1 where for illustration purposes, features are only shown in 1-D and 2-D, and only two-class problems are considered. In the case of FS-1, the SVM with a polynomial kernel in quadratic form would make the proper transformation into 3-D so that the new (transformed) features are linearly separable. However, for FS-2, a sinusoid with the right frequency, $f$, may be used instead. Therefore, especially in real and complex problems, a high level of operational diversity, which can only enable the right (set of) transformations, is of paramount importance.

In biological learning systems, this is addressed in the neuron cell level. For example, FIG. 2, illustrates a biological neuron (left) with the direction of the signal flow, and a synapse (right) in the mammalian nervous system. Each neuron conducts the electrical signal over three distinct operations: 1) synaptic connections in dendrites, an individual operation over each input signal from the synapse connection of the input neuron's axon terminals; 2) a pooling operation of the operated input signals via spatial and temporal signal integrator in the soma; and 3) an activation in the initial section of the axon or the so-called axon hillock. If the pooled potentials exceed a certain limit, the axon "activates" a series of pulses (called action potentials).

As shown in the right side of FIG. 2, each terminal button may be connected to other neurons across a small gap called a synapse. The physical and neurochemical characteristics of each synapse determine the signal operation which is non-linear in general along with the signal strength and polarity of the new input signal. Information storage or processing is concentrated in the cells' synaptic connections or more precisely through certain operations of these connections together with the connection strengths (weights). Such biological neurons or neural systems in general are built from a large diversity of neuron types varying entirely or partially structural, biochemical, and electrophysiological properties. For instance in the mammalian retina, there are roughly 55 different types of neurons to perform the low-level visual sensing. The functions of the 22 of them are already known and a cell defined as a "type" by structural criteria carries out a distinct and individual physiological function (operator). Accordingly in neurological systems, several distinct operations with proper weights (parameters) are created to accomplish such diversity and trained in time to perform or "to learn" many neural functions. Neural networks with higher diversity of computational operators have more computational powers and it is also a fact that adding more neural diversity allows the network size and total connections to be reduced.

Conventional ANNs were designed to simulate biological neurons. However, at the best ANN models are based only loosely on biology. The most typical ANN neuron model is McCulloch-Pitts which is mainly used in many feed-forward ANNs such as multi-layer perceptrons (MLPs). As in Eq. (1) shown below, in this formal model, an artificial neuron performs linear summation scaled with the synaptic weights. Thus, the synaptic connections with distinct neurochemical operations and the integration in the soma are modeled solely as a linear transformation, or in other words, the linear weighted sum, followed by a possibly non-linear thresholding function, $f(.)$, also called the activation function.

$$x_k^l = b_k^l + \Sigma w_{jk}^{l-1} y_j^{l-1} \text{ and } y_k^l = f(x_k^l) \quad (1)$$

From Eq. (1), this model is a limited and crude model of the biological neurons, which is one of the reasons that render ANNs having a high variation on their learning and generalization performances in many problems. There have been some attempts to modify MLPs by changing the neuron model and/or conventional back-propagation (BP) algorithm. However, their performance improvements were not significant in general. Even though the network topology or the parameter updates were optimized according to the problem in hand, such approaches still inherit the main drawback of MLPs. For example, they employ the conventional neuron model described in Eq. (1). This is also true for other ANN topologies such as recurrent neural networks, long short-term memory networks, and convolutional neural networks.

Another feed-forward and fully-connected ANNs is the Radial Basis Functions (RBFs), which employ a set of RBFs, each of which is embedded in a hidden neuron. The most typical RBF is Gaussian and, thanks to this non-linear operator RBF networks promise a faster learning capability than the MLPs. However, they still suffer from the same major problem of incapability to approximate certain functions or discriminate certain patterns unless (sometimes infeasibly) large network configuration is used because they use only one operator, the RBF, regardless of the problem in hand.

There is a need, therefore for addressing this drawback and achieving a more generalized model of biological neurons. There is also a need for providing a method of searching for the best operators for each layer individually; otherwise the search space for a GOP with several hidden layers can be unfeasibly large.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

SUMMARY OF THE INVENTION

One embodiment may be directed to a method that may include receiving data at an input neural node of an input layer, the received data corresponding to a learning objective that is to be accomplished. The method may also include initializing a final POP by assigning the input layer as an input layer of a maximum POP configuration (POPmax). The method may further include forming a 3-layer, single hidden layer multi-layered progressive operational perceptron ($1^{st}$ GOPmin) using the configuration of the input layer, a first hidden layer and an output layer of the POPmax. The method may also include inserting the formed hidden layer of the $1^{st}$ GOPmin as a first hidden layer of the final POP, generating learning performance statistics of the $1^{st}$ GOPmin, and determining if the learning objective can be achieved with the $1^{st}$ GOPmin. If the learning objective is achieved, the formation process may be terminated. Otherwise, if the learning objective cannot be achieved with the $1^{st}$ GOPmin, the method may include using a previous hidden layer's output as the input layer by forward propagating training data, forming a second 3-layer, single hidden layer multi-layered progressive operational perceptron ($2^{nd}$ GOPmin) using the configurations of a second hidden layer of the POPmax as the hidden layer and the output layer of the, POPmax, as the output layer. The method may also include forming the $2^{nd}$GOPmin and inserting the formed hidden layer of the $2^{nd}$GOPmin as the $2^{nd}$ hidden layer of the final POP. In addition, the method may include generating learning performance statistics of the $2^{nd}$ GOPmin. The method may further include checking if a target performance is achieved or not with the $2^{nd}$ GOPmin, and if not achieved, repeat: forming, checking and inserting in the same order for a third, fourth, and additional GOPmin, until the target performance is achieved or all hidden layers of POPmax are formed. The method may also include forming the output layer of the final POP as the output layer of the last GOPmin formed.

In an embodiment, the formation of the first hidden layer and additional hidden layers and the output layer may include determining optimal operators and parameters for neural nodes contained therein. In another embodiment, when it is determined that the learning objective can be achieved with the first hidden layer, the method may further include appending the first hidden layer to a final multi-layered progressive operation perceptron as its first hidden layer. In a further embodiment, the formation of the first hidden layer and additional hidden layers may be carried out by a greedy iterative search. In yet another embodiment, the greedy iterative search may include performing a layerwise evaluation by sequentially assigning one operator set to all neural nodes of the first hidden layer and the additional hidden layers.

Another embodiment may be directed to an apparatus. The apparatus may include at least one memory including computer program code, and at least one processor. The at least one memory and the computer program code may be configured, with the at least one processor, to cause the apparatus at least to receive data at an input neural node of an input layer, the received data corresponding to a learning objective that is to be accomplished. The at least one memory and the computer program code may also be configured, with the at least one processor, to cause the apparatus at least to form a 3-layer, single hidden layer multi-layered progressive operational perceptron ($1^{st}$ GOPmin) using the first hidden layer and the output layer of the maximum POP configuration, (POPmax). The at least one memory and the computer program code may further be configured, with the at least one processor, to cause the apparatus at least to determine if the learning objective can be achieved with the first hidden layer. The at least one memory and the computer program code may also be configured, with the at least one processor, to cause the apparatus at least to, if the learning objective cannot be achieved with the first hidden layer, use a previous hidden layer's output as the input layer, forming a second 3-layer, single hidden layer multi-layered progressive operational perceptron ($2^{nd}$ GOPmin) using the second hidden layer as the only hidden layer and the output layer of the POPmax. The at least one memory and the computer program code may further be configured, with the at least one processor, to cause the apparatus at least to train the $2^{nd}$ GOPmin and check if a target performance is achieved or not, and if not achieved, repeat the training and checking until the target performance is achieved or all hidden layers of POPmax are formed. The at least one memory and the computer program code may also be configured, with the at least one processor, to cause the apparatus at least to form an output layer corresponding to the first hidden layer and any additional hidden layers, and generate learning performance statistics based on the received data.

In an embodiment, the formation of the first hidden layer and the additional hidden layers may include determining optimal operators and parameters for neural nodes contained therein. In another embodiment, when it is determined that the learning objective can be achieved with the first hidden layer, the at least one memory and the computer program code may further be configured, with the at least one processor, to cause the apparatus at least to append the first hidden layer to a final layer of the multi-layered progressive operation perceptron. In yet another embodiment, the formation of the first hidden layer and the additional hidden layers may be carried out by a greedy iterative search. In a further embodiment, the greedy iterative search may include performing a layerwise evaluation by sequentially assigning one operator set to all neural nodes of the first hidden layer and the additional hidden layers.

Another embodiment may be directed to a computer program, embodied on a non-transitory computer readable medium, the computer program, when executed by a processor, causes the processor to receive data at an input neural node of an input layer, the received data corresponding to a learning objective that is to be accomplished. The computer program, when executed by the processor, may also cause the processor to form a 3-layer, single hidden layer multi-layered progressive operational perceptron ($1^{st}$ GOPmin) using a first hidden layer and an output layer of a maximum POP configuration, (POPmax). The computer program, when executed by the processor, may further cause the processor to determine if the learning objective can be achieved with the first hidden layer. The computer program, when executed by the processor, may also cause the processor to, if the learning objective cannot be achieved with the first hidden layer, use a previous hidden layer's output as the input layer, forming a second 3-layer, single hidden layer multi-layered progressive operational perceptron ($2^{nd}$ GOPmin) using a second hidden layer as the only hidden layer and the output layer of the POPmax. The computer program, when executed by the processor, may also cause the processor to train the $2^{nd}$ GOPmin and check if a target performance is achieved or not, and if not achieved, repeat the training and checking until the target performance is achieved or all hidden layers of POPmax are formed. The computer program, when executed by the processor, may further cause the processor to form an output layer corresponding to the first hidden layer and any additional hidden layers, and generate learning performance statistics based on the received data.

In an embodiment, the formation of the first hidden layer and the additional hidden layers may include determining optimal operators and parameters for neural nodes contained therein. In another embodiment, when it is determined that the learning objective can be achieved with the first hidden layer, the computer program, when executed by a processor, may further cause the processor to append the first hidden layer to a final layer of the multi-layered progressive operation perceptron. In yet another embodiment, the formation of the first hidden layer and the additional hidden layers may be carried out by a greedy iterative search. In a further embodiment, the greedy iterative search may include performing a layerwise evaluation by sequentially assigning one operator set to all neural nodes of the first hidden layer and the additional hidden layers.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings:

FIG. 12 illustrates a system, according to certain embodiments.

Figure 1:
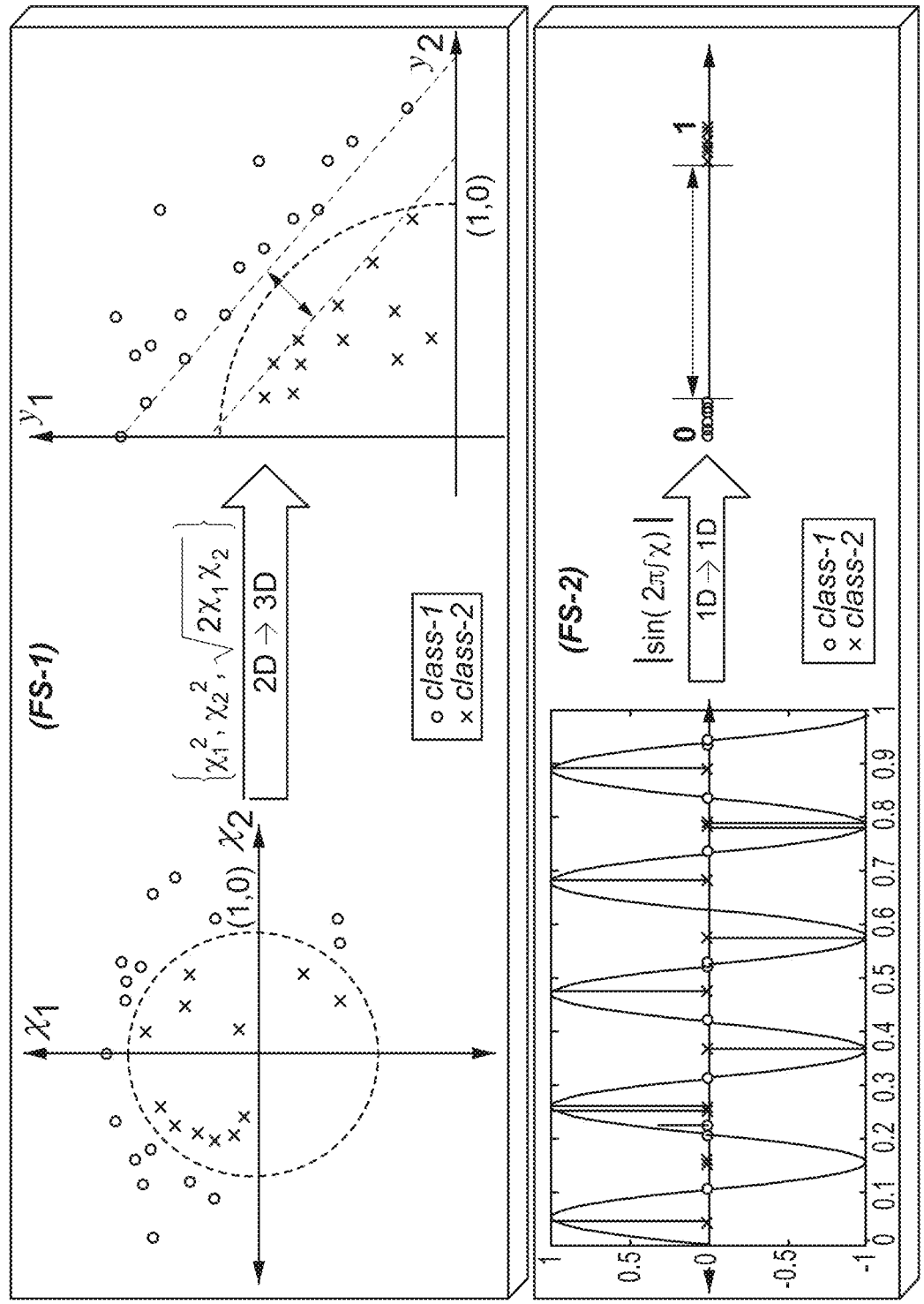
FIG. 1 illustrates a two sample feature synthesis performed on 2-D (FS-1) and 1-D (FS-2) feature spaces.
Figure 2:
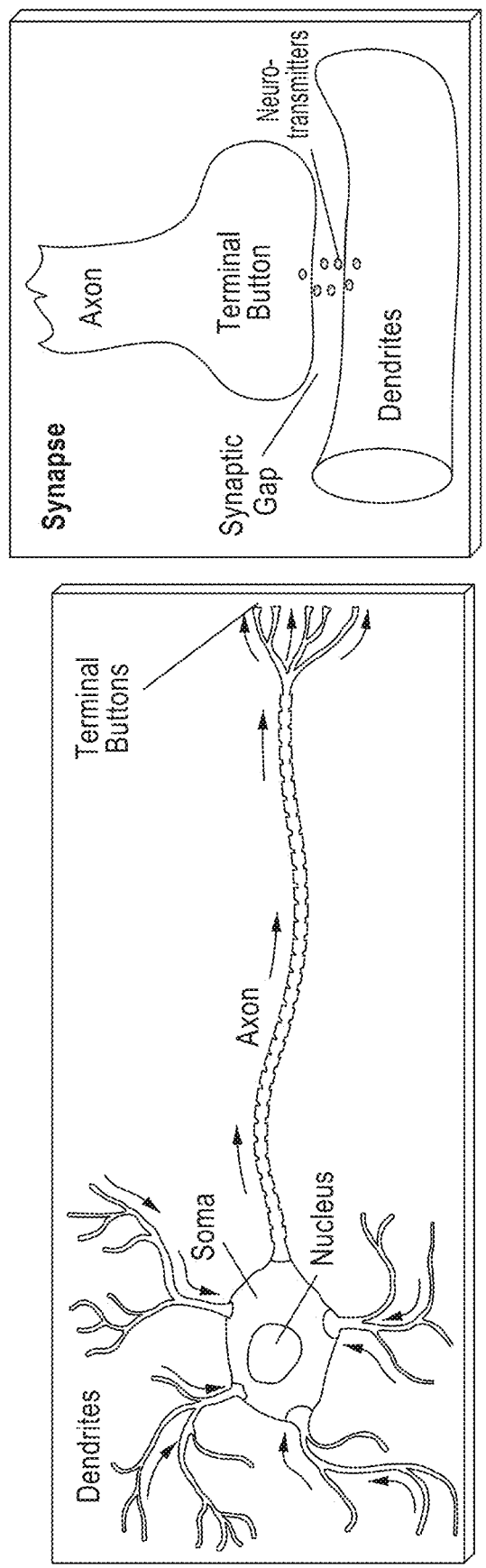
FIG. 2 illustrates a biological neuron (left) with the direction of the signal flow, and a synapse (right).

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical or structural changes may be made to the invention without departing from the spirit or scope of this disclosure. To avoid detail not necessary to enable those skilled in the art to practice the embodiments described herein, the description may omit certain information known to those skilled in the art. The following detailed description is, therefore, not to be taken in a limiting sense.

DETAILED DESCRIPTION

The features, structures, or characteristics of the invention described throughout this specification may be combined in any suitable manner in one or more embodiments. For example, the usage of the phrases "certain embodiments," "some embodiments," or other similar language, throughout this specification refers to the fact that a particular feature, structure, or characteristic described in connection with the embodiment may be included in at least one embodiment of the present invention.

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical or structural changes may be made to the invention without departing from the spirit or scope of this disclosure. To avoid detail not necessary to enable those skilled in the art to practice the embodiments described herein, the description may omit certain information known to those skilled in the art. The following detailed description is, therefore, not to be taken in a limiting sense.

The examples described herein are for illustrative purposes only. As will be appreciated by one skilled in the art, certain embodiments described herein, including, for example, but not limited to, those shown in FIGS. 1-11, may be embodied as a system, apparatus, method, or computer program product. Accordingly, certain embodiments may take the form of an entirely software embodiment or an embodiment combining software and hardware aspects. Software may include but is not limited to firmware, resident software, or microcode. Furthermore, other embodiments may take the form of a computer program product accessible from a computer-usable or computer-readable medium providing program code for use by or in connection with a computer or any instruction execution system.

Any combination of one or more computer usable or computer readable medium(s) may be utilized in certain embodiments described herein. For the purposes of this description, a computer-usable or computer readable medium can be any apparatus that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may independently be any suitable storage device, such as a non-transitory computer-readable medium. Suitable types of memory may include, but not limited to: a portable computer diskette; a hard disk drive (HDD), a random access memory (RAM), a read-only memory (ROM); an erasable programmable read-only memory (EPROM or Flash memory); a portable compact disc read-only memory (CDROM); and/or an optical storage device.

The memory may be combined on a single integrated circuit as a processor, or may be separate therefrom. Furthermore, the computer program instructions stored in the memory may be processed by the processor can be any suitable form of computer program code, for example, a compiled or interpreted computer program written in any suitable programming language. The memory or data storage entity is typically internal, but may also be external or a combination thereof, such as in the case when additional memory capacity is obtained from a service provider. The memory may also be fixed or removable.

The computer usable program code (software) may be transmitted using any appropriate transmission media via any conventional network. Computer program code, when executed in hardware, for carrying out operations of certain embodiments may be written in any combination of one or more programming languages, including, but not limited to, an object oriented programming language such as Java, Smalltalk, C++, C# or the like and conventional procedural programming languages, such as the "C" programming language or similar programming languages. Alternatively, certain embodiments may be performed entirely in hardware.

Depending upon the specific embodiment, the program code may be executed entirely on a user's device, partly on the user's device, as a stand-alone software package, partly on the user's device and partly on a remote computer, or entirely on the remote computer or server. In the latter scenario, the remote computer may be connected to the user's device through any type of conventional network. This may include, for example, a local area network (LAN) or a wide area network (WAN), Bluetooth, Wi-Fi, satellite, or cellular network, or the connection may be made to an external computer (for example, through the Internet using an Internet Service Provider).

According to certain embodiments, it may be possible to address the various drawbacks described above, and achieve a more generalized model of biological neurons. In certain embodiments, this may be accomplished by presenting GOPs that can encapsulate many linear and non-linear operators. Contrary to MLPs, each neuron in a GOP can perform a distinct operation over its input signals. This mimics a biological neuron cell with distinct neurochemical characteristics of its synaptic connections each with a certain strength (weight). A neuron (node) has only one operator and hence it is called the nodal operator that uses the same function but with a different parameter (weight) for each neuron connection from the previous layer.

In certain embodiments, the outputs of the nodal operators may be integrated with a pooling operator, which contrary to MLPs, can be any proper integrator besides summation. A similar flexibility may also be allowed for the activation operator (function). Thus, each GOP neuron can have any operator set (nodal, pool, and activation) where each operator is selected among a library of operators to maximize the learning or the generalization performance. Finally, as in MLPs a GOP can be homogenous where all neurons have the same set of operators (only the network parameters vary), or heterogeneous where each neuron can have different set of operators, either randomly selected or properly searched to maximize the diversity and hence the learning performance.

According to certain embodiments, finding the optimal operator set for each neuron is crucial for GOPs. According to other embodiments, GOPs can be formed using alternative ways. In certain embodiments, a minimal depth GOP with the least number of hidden layers may be designed, while it can learn a complex problem with the desired accuracy. In order to achieve this, POPs may be proposed. POPs, according to certain embodiments, may be heterogeneous GOPs that are self-organized and depth-adaptive according to the learning problem. As the name implies, they may be created progressively, layer by layer, while the operators and parameters of each layer are optimized within a distinct and single hidden layer GOP using a greedy iterative search (GIS). A hidden layer may be formed (best operator set may be searched and parameters optimized for each hidden neuron) by GIS and integrated into the current POP only if it cannot achieve the learning objective in its current form. This approach enables searching for the best operators for each layer individually. Otherwise the search space for a GOP with several hidden layers may be unfeasibly large.

Generalized Operational Perceptrons (GOPs)

A. Overview

Figure 3:
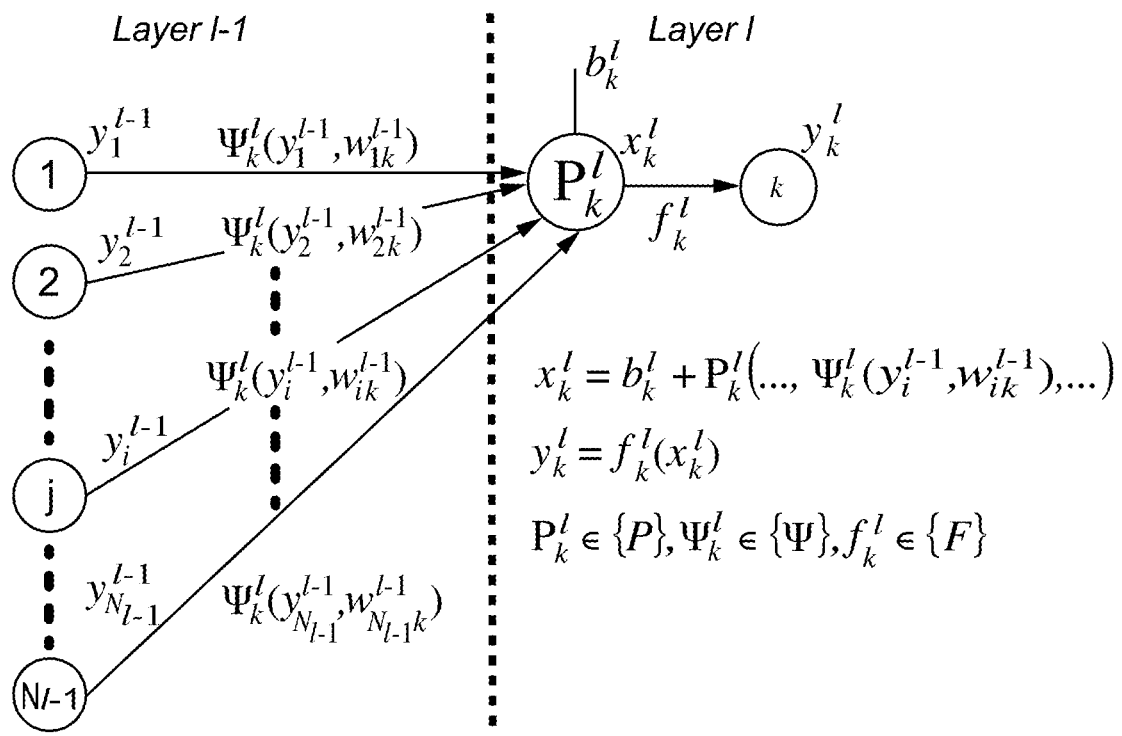
FIG. 3 illustrates a formation of a GOP neuron at layer-l from the outputs of the previous layer's neurons, according to certain embodiments.

FIG. 3 illustrates a formation of a GOP neuron at layer-l from the outputs of the previous layer's neurons, according to certain embodiments. As illustrated in FIG. 3, the $i^{th}$ GOP neuron at layer l+1 has three operators: nodal operator, $\Psi_i^{l+1}$, pooling operator, $P_i^{l+1}$, and finally the activation operator, $f_i^{l+1}$. It may be assumed that each operator is selected among a library of potential operators, $P_i^{l+1} \in \{P\}$, $\Psi_i^{l+1}, f_i^{l+1} \in \{F\}$. For example, the nodal operator library, $\{\Psi\}$, can be composed of by, but not limited to, the following operators: multiplication, exponential, harmonic (sinusoid), quadratic function, Gaussian, Derivative of Gaussian (DoG), Laplacian, and Hermitian. Similarly, the pool operator library, $\{P\}$, can include, but not limited to: summation, n-correlation, maximum, and median. In certain embodiments, typical activation functions that suit to classification problems may be combined within the activation operator library, $\{F\}$, composed of, but not limited to, for example, tan h, linear, and binary.

B. Back Propagation for GOPs

According to certain embodiments, for an L-layer GOP, let l=1 and l=L be the input (In) and output (Out) layers, respectively. The minimum squared error (MSE) in the output layer can be written as:

$$E = E(y_1^L, \ldots, y_{N_L}^L) = \frac{1}{N_L} \sum_{i=1}^{N_L} (y_i^L - t_i)^2 \tag{2}$$

For an input vector p, and its corresponding output vector, $[y_1^L, \ldots, y_{N_L}^L]$, the derivative of this error may be computed with respect to an individual weight (connected to that neuron, k) and bias (of the neuron k), $w_{ik}^l$ and $b_k^l$, so that a gradient descent method may be performed to minimize the error accordingly:

$$\frac{\partial E}{\partial w_{ik}^l} = \frac{\partial E}{\partial x_k^l} \frac{\partial x_k^l}{\partial w_{ik}^l} \text{ and } \frac{\partial E}{\partial b_k^l} = \frac{\partial E}{\partial x_k^l} \frac{\partial x_k^l}{\partial b_k^l} = \frac{\partial E}{\partial x_k^l} \quad (3)$$

In certain embodiments, both derivatives may depend on the sensitivities of the error to the input, $x_k^l$. These sensitivities may usually be called as delta errors. In particular, $\Delta_k^l = \partial E/\partial x_k^l$ be the delta error of the $k^{th}$ neuron at layer l. The delta error may be written by one step backward propagation from the output of that neuron, $y_k^l$, which contributes all the neurons' inputs in the next layer, such as for example:

$$\Delta_k^l = \frac{\partial E}{\partial x_k^l} = \frac{\partial E}{\partial y_k^l} \frac{\partial y_k^l}{\partial x_k^l} = \frac{\partial E}{\partial y_k^l} f'(x_k^l) \quad (4)$$

The moment that the sensitivities of the error to the output, $\partial E/\partial x_k^l$, were found, the delta error may be found. For the output layer, l=L, both terms may be known:

$$\Delta_k^L = \frac{\partial E}{\partial x_k^L} = f'(x_k^L)(y_k^L - t_k) \quad (5)$$

In consideration of the GOP in FIG. 3, the output of the previous layer neuron may be set as, $y_k^l$, which contributes all the neurons' inputs in the next layer, for example:

$$x_1^{l+1} = b_1^{l+1} + P_1^{l+1}(\Psi_1^{l+1}(w_{11}^{l+1}, y_1^l), \ldots, \Psi_1^{l+1}(w_{k1}^{l+1}, y_k^l), \ldots)$$

$$x_i^{l+1} = b_i^{l+1} + P_i^{l+1}(\Psi_i^{l+1}(w_{1i}^{l+1}, y_1^l), \ldots, \Psi_i^{l+1}(w_{ki}^{l+1}, y_k^l), \ldots)$$

$$x_{N_{l+1}}^{l+1} = b_{N_{l+1}}^{l+1} + P_{N_{l+1}}^{l+1}(\Psi_{N_{l+1}}^{l+1}(w_{1N_{l+1}}^{l+1}, y_1^l), \ldots, \Psi_{N_{l+1}}^{l+1}(w_{kN_{l+1}}^{l+1}, y_k^l), \ldots) \quad (6)$$

In view of Eq. (6), the output of the $k^{th}$ neuron in the previous layer, $y_k^l$, contributes to the input of the neurons of the current layer with individual weights, $w_{ki}^{l+1}$. With this in mind, it is possible to write the sensitivities of the error to the output, $\partial E/\partial x_k^l$, as follows:

$$\frac{\partial E}{\partial y_k^l} = \quad (7)$$

$$\sum_{i=1}^{N_{l+1}} \frac{\partial E}{\partial x_i^{l+1}} \frac{\partial x_i^{l+1}}{\partial y_k^l} = \sum_{i=1}^{N_{l+1}} \Delta_i^{l+1} \frac{\partial x_i^{l+1}}{\partial P_i^{l+1}} \frac{\partial P_i^{l+1}}{\partial \Psi_i^{l+1}(w_{ki}^{l+1}, y_k^l)} \frac{\partial \Psi_i^{l+1}(w_{ki}^{l+1}, y_k^l)}{\partial y_k^l}$$

Where $$\partial x_i^{l+1} / \partial P_i^{l+1} = 1.$$

Let $\nabla_{\Psi_{ki}} P_i^{l+1} = \frac{\partial P_i^{l+i}}{\partial \Psi_i^{l+1}(w_{ki}^{l+1}, y_k^l)}.$ and, $\nabla_y \Psi_{ki}^{l+1} = \frac{\partial \Psi_i^{l+i}(w_{ki}^{l+1}, y_k^l)}{\partial y_k^l}.$ Then Eq. (7) becomes:

$$\frac{\partial E}{\partial y_k^l} = \sum_{i=1}^{N_{l+1}} \Delta_i^{l+1} \nabla_{\Psi_{ki}} P_i^{l+1} \nabla_y \Psi_{ki}^{l+1} \quad (8)$$

In certain embodiments, both $\nabla_{\Psi_{ki}} P_i^{l+1}$ and $\nabla_y \Psi_i^{l+1}$ will be different functions for different nodal and pooling operators. From the output sensitivity, $\partial E/\partial x_k^l$, the process of obtaining the delta of that neuron, $\Delta_k^l$, which leads to the generic equation of the back-propagation of the deltas for GOPs, may be as follows:

$$\Delta_k^l = \frac{\partial E}{\partial x_k^l} = \frac{\partial E}{\partial y_k^l} f'(x_k^l) = f'(x_k^l) \sum_{i=1}^{N_{l+1}} \Delta_i^{l+1} \nabla_{\Psi_{ki}} P_i^{l+1} \nabla_y \Psi_{ki}^{l+1} \quad (9)$$

Once all the deltas in each layer are formed by back-propagation, then weights and bias of each neuron can be updated by the gradient descent method. Specifically the delta of the $k^{th}$ neuron at layer l, $\Delta_k^l$ may be used to update the bias of that neuron and all weights of the neurons in the previous layer connected to that neuron. The bias update in GOPs may be identical as for MLPs:

$$\frac{\partial E}{\partial b_k^l} = \Delta_k^l \quad (10)$$

For the weight sensitivity, the chain rule of derivatives may be written as, $$\frac{\partial E}{\partial w_{ki}^{l+1}} = \frac{\partial E}{\partial x_i^{l+1}} \frac{\partial x_i^{l+1}}{\partial w_{ki}^{l+1}} = \Delta_i^{l+1} \frac{\partial x_i^{l+1}}{\partial P_i^{l+1}} \frac{\partial P_i^{l+1}}{\partial \Psi_i^{l+1}(w_{ki}^{l+1}, y_k^l)} \frac{\partial \Psi_i^{l+1}(w_{ki}^{l+1}, y_k^l)}{\partial w_{ki}^{l+1}} \quad (11)$$

where $$\partial x_i^{l+1} / \partial P_i^{l+i} = 1. \text{ Let } \nabla_w \Psi_{ki}^{l+1} = \frac{\partial \Psi_i^{l+i}(w_{ki}^{l+1}, y_k^l)}{\partial y_{ki}^{l+1}}.$$

Then Eq. (11) simplifies to, $$\frac{\partial E}{\partial w_{ki}^{l+1}} == \Delta_i^{l+1} \nabla_{\Psi_{ki}} P_i^{l+1} \nabla_w \Psi_{ki}^{l+1} \quad (12)$$

Table 1 presents some sample nodal operators along with their derivatives, according to certain embodiments, $\nabla_w \Psi_{ki}^{l+1}$ and $\nabla_y \Psi_{ki}^{l+1}$ with respect to the weight, $w_{ki}^{l+1}$, and the output, $y_k^l$ of the previous layer neurons. Similarly, Table 2 presents some typical pooling operators and their derivatives with respect to the output of the $i^{th}$ neuron's nodal operator at layer, l+1 over the weight, $w_{ki}^{l+1}$, and the output, $y_k^l$, of the $k^{th}$ neuron in the previous layer. Using these lookup tables, the error on the output layer may be back-propagated and weight sensitivities can be computed. BP iterations may be run iteratively to update the weights (the parameters of the nodal operators) and biases of each neuron in the GOP until a stopping criterion has been met such as maximum number of iterations (iterMax), or the target learning objective. As a result, the algorithm for the BP training of GOPs is given in Table 3.

According to certain embodiments, the BP training may be independent from the operator search. In other words, a GOP may be trained by BP only after an operator set has been assigned to each neuron of the network. The BP training for GOPs may be a gradient descent method just like the traditional BP for MLPs. Therefore, both BP operations

TABLE 1

Nodal operators and derivatives

| Description | $\Psi_{ki}^{l+1}(w_{ki}^{l+1}, y_k^l)$ | $\nabla_w \Psi_{ki}^{l+1}$ | $\nabla_y \Psi_{ki}^{l+1}$ |
|---|---|---|---|
| 0 Multiplication | $w_{ki}^{l+1} y_k^l$ | $y_k^l$ | $w_{ki}^{l+1}$ |
| 1 Exponential | $\exp(w_{ki}^{l+1} y_k^l) - 1$ | $y_k^l \exp(w_{ki}^{l+1} y_k^l)$ | $w_{ki}^{l+1} \exp(w_{ki}^{l+1} y_k^l)$ |
| 2 Harmonic | $\sin(w_{ki}^{l+1} y_k^l)$ | $y_k^l \cos(w_{ki}^{l+1} y_k^l)$ | $w_{ki}^{l+1} \cos(w_{ki}^{l+1} y_k^l)$ |
| 3 Quadratic | $w_{ki}^{l+1} (y_k^l)^2$ | $(y_k^l)^2$ | $2 w_{ki}^{l+1} y_k^l$ |
| 4 Gaussian | $w_{ki}^{l+1} \exp(-w_{ki}^{l+1} (y_k^l)^2)$ | $(1 - w_{ki}^{l+1} (y_k^l)^2) \exp(-w_{ki}^{l+1} (y_k^l)^2)$ | $(-2(w_{ki}^{l+1})^2 y_k^l) \exp(-w_{ki}^{l+1} (y_k^l)^2)$ |
| 5 DoG | $w_{ki}^{l+1} y_k^l \exp(-w_{ki}^{l+1} (y_k^l)^2)$ | $y_k^l (1 - w_{ki}^{l+1} (y_k^l)^2) \exp(-w_{ki}^{l+1} (y_k^l)^2)$ | $w_{ki}^{l+1} (1 - 2(w_{ki}^{l+1})^2 y_k^l) \exp(-w_{ki}^{l+1} (y_k^l)^2)$ |

TABLE 2

Pool operators and derivatives

| Description | $P_i^{l+1}(\ldots, \Psi_i^{l+1}(w_{ki}^{l+1}, y_k^l), \ldots)$ | $\nabla_{\Psi_{ki}} P_i^{l+1}$ |
|---|---|---|
| 0 Summation | $\sum_{k=1}^{N_l} \Psi_i^{l+1}(w_{ki}^{l+1}, y_k^l)$ | 1 |
| 1 1n-Correlation (if $N_l := 2$) | $\sum_{k:=2}^{N_l} \Psi_i^{l+1}(w_{ki}^{l+1}, y_k^l) \Psi_i^{l+1}(w_{k+1i}^{l+1}, y_{k+1}^l)$ | $\Psi_i^{l+1}(w_{k+1i}^l, y_{k+1}^l)$ |
| 2 2n-Correlation (if $N_l := 3$) | $\sum_{k:=3}^{N_l} \Psi_i^{l+1}(w_{ki}^{l+1}, y_k^l) \Psi_i^{l+1}(w_{k+1i}^{l+1}, y_{k+1}^l) \Psi_i^{l+1}(w_{k+2i}^{l+1}, y_{k+2}^l)$ | $\Psi_i^{l+1}(w_{k+1i}^{l+1}, y_{k+1}^l) \Psi_i^{l+1}(w_{k+2i}^{l+1}, y_{k+2}^l)$ |
| 3 Maximum | $\max_k \Psi_i^{l+1}(w_{ki}^{l+1}, y_k^l)$ | $\begin{cases} 1 & \text{if argmax}(P_i^{l+1}) = k \\ 0 & \text{else} \end{cases}$ |

TABLE 3

Back-Propagation algorithm for GOPs

Input: GOP, Stopping Criteria (iterMax, . . . )
Output: BP trained GOP = BP(GOP)

1) Initialize weights (usually randomly, U(−a, a)) of GOP
2) UNTIL a stopping criterion is reached ITERATE:
. For each item (or a group of items or all items) in the train dataset, DO:
   i. FP: Forward propagate from the input layer to the output layer to find outputs of each neuron at each layer, $y_k^l$.
   ii. BP: Compute delta error at the output layer and back-propagate it to first hidden layer to find out all the delta errors.
   iii. PP: Find the weight and bias sensitivities as in Eqs. (10) and (12) (cumulate them for Batch learning)
   iv. Update: Update the weights and biases with the (cumulation of) sensitivities found in previous step scaled with the learning factor, ε:

$$w_{ki}^{l+1}(t+1) = w_{ki}^{l+1}(t) - \varepsilon \frac{\partial E}{\partial w_{ki}^{l+1}} \quad (13)$$

$$b_i^{l+1}(t+1) = b_i^{l+1}(t) - \varepsilon \frac{\partial E}{\partial b_i^{l+1}}$$

may suffer equally from possible early convergence to a local minimum and multiple BP runs are usually required for a better convergence.

Although the GOPs may be homogeneous as MLPs where one operator set is assigned to the entire network, this may significantly limit the diversity of the network. According to certain embodiments, it may be possible to form a highly divergent heterogeneous GOP where the parameters and the operators for each neuron are optimized according to the problem at hand, so that each hidden layer may perform the right transformation over the complex pattern of the previous layer outputs to maximize the learning objective at the output layer. This may require a thorough search for the right operators along with the training of the entire network to find out the right parameters. However, finding out the right operators even for a single neuron may eventually require a trained network to evaluate the learning performance. Furthermore, the optimality of the operator set of that neuron may depend on the operators of the other neurons since variations in the latter may drastically change the optimality of the earlier operator choice for that neuron. Such problems may be addressed by a progressive formation approach.

Progressive Operational Perceptrons (POPs)

According to certain embodiments, let $\Theta$ be the operator library that contains all possible operator sets. In a multi-layer heterogeneous GOP, considering the depth and size of the network and the number of operator set alternatives in $\Theta$, a sequential search for finding out the operator set for each neuron may be computationally infeasible due to the massive size of such combinatorial search space. This, therefore, may be one, out of various others, the main motivation behind the POPs. In certain embodiments, starting from the first hidden layer, each hidden layer of the final POP (the target multi-layer heterogeneous GOP) may be formed individually, and the next hidden layer may only be formed if the target learning objective could not be achieved so far with the current POP. The latter provides an explanation why POPs are depth-adaptive, as they only get deeper when the learning problem could not be solved with the current POP. Without loss of generality it may be assumed that a max-depth POP topology with hmax hidden layers, POPmax may be defined in advance for at least two reasons: 1) to put a practical depth limit for the progressive formation, and 2) the final POP can be formed according to its layer topology (e.g. number of neurons in each layer) and with a depth (number of layers) less than or equal to the maximum depth. Therefore, POPmax may be a configuration template for the final POP.

In certain embodiments, the formation of each hidden layer, h, may be optimized in a distinct and minimal-depth GOP, GOPmin(h), with only a single hidden layer and the output layer that are the corresponding hidden and output layers of the POPmax. The objective is to form both hidden and output layers in such a way that maximizes the learning performance. Further, the formation of a layer may involve both finding out the optimal operators and their parameters for its neurons. In this minimal-depth network a sequential and iterative search using short BP training runs may be both feasible and significantly easier for finding the optimal operator sets.

According to certain embodiments, for the formation of the first hidden layer, the input and output layer configuration (i.e., the number of neurons) of the POPmax may be identical for the GOPmin(1). While forming both hidden and output layers within the GOPmin(1), an investigation as to whether the learning objective can be achieved by this GOP is performed. If so, the formed GOPmin(1) with the optimal operators and parameters may be the final POP, and the progressive formation can be terminated without forming other hidden layers. Otherwise, the formed hidden layer within GOPmin(1) may be appended into the final POP as the first hidden layer, the output of which will be used as the input layer of the GOPmin(2) that will then be used to form the second hidden layer. In other words, the second hidden layer may be formed within the GOPmin(2) whose input layer is the (neuron outputs of the) first hidden layer that is formed earlier within GOPmin(1). To compute these neuron outputs, the training data may be forward propagated within GOPmin(1). If the learning objective is achieved when the GOPmin(2) is formed, then it may be hidden, and output layers may then be used as the second hidden and the output layers of the final POP, and the progressive search may be terminated without forming other hidden layers. Otherwise, the progressive formation may continue with the third hidden layer formation and so on until either the learning objective is achieved or the last hidden layer of the POPmax is formed within the corresponding GOPmin(hmax).

Figure 4:
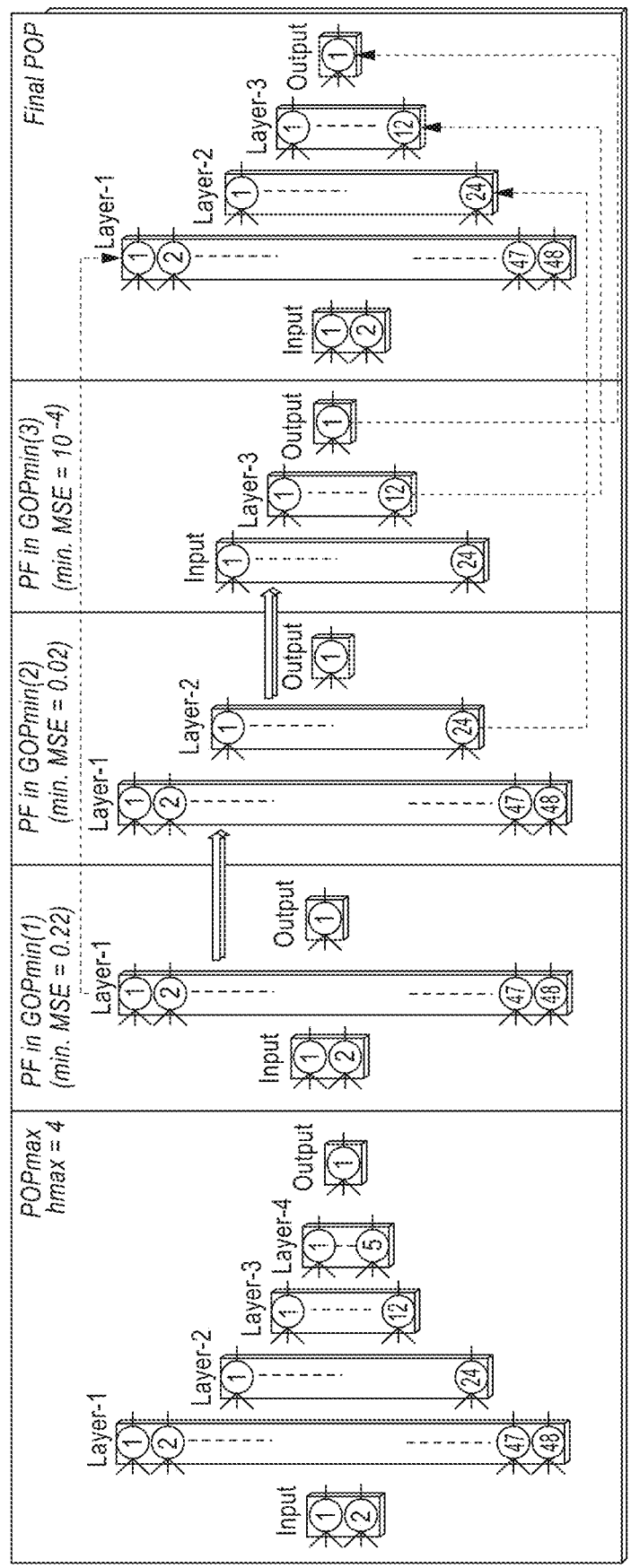
FIG. 4 illustrates a sample progressive formation of a 3 hidden layer POP from a 4 hidden layer POPmax, according to certain embodiments.

FIG. 4 illustrates a sample progressive formation of a 3-hidden layer POP from a 4 hidden layer (hmax=4) POPmax, according to certain embodiments. Since the learning objective may be achieved after the GOPmin(3) is formed, the final POP may only have 3 hidden layers. In certain embodiments, the learning objective that is optimized during the progressive formation of the hidden and output layers in each GOPmin depends on the learning problem. For instance the optimality criterion for classification may be defined such as minimum MSE or CE in train or validation datasets. Alternatively, in case of binary classification problems, it may be maximum Precision (P), Recall (R) or the F1 measure, $F1=2PR/(P+R)$, measures selected according to the classification problem in hand.

The progressive formation in each GOPmin may find the optimal operator set for each hidden neuron. For this purpose a sequential search by evaluating each operator set in $\Theta$ individually for each hidden neuron may still have an infeasible computational complexity. It may also be probable that for any layer, searching for different optimal operator sets for its neurons might be redundant. For instance for classification, the optimal operator set for a neuron at layer l, may make that neuron output as the most informative (i.e. achieves the highest discrimination among the classes) for the input pattern from the previous layer neurons' outputs. Since the input pattern of each neuron at layer l is identical (i.e., the pattern present at the outputs of the neurons in the layer l−1), the optimal operator set for one neuron may also be optimal for the other neurons at layer l. Therefore, the search operation may be limited by assigning one operator set to all the neurons at a particular layer. Still the alternative may also be tried by assigning random operator sets to both layers (hidden and output) neurons and performing a few short BP test-runs to evaluate the learning performance of the GOPmin.

Starting at this assignment (and evaluation), then the progressive formation of the hidden layer may be carried out by a greedy iterative search (GIS) that performs layerwise evaluation by sequentially assigning one operator set in $\Theta$ to all neurons of a layer in that GOPmin while keeping the other layer as is. GIS may start with initially assigning random operator sets to both layers and initial evaluation of this assignment to verify whether the aforementioned redundancy assumption holds. Once an operator set is assigned to a layer, by running few BP test-runs, the operator set may be evaluated with respect to the learning objective. At the end of the evaluation of all sets in $\Theta$ for the layer l, the best performing operator set, $\Theta^*_l$, may then be assigned to all the neurons of that layer, and the GIS may iterate on the other layer.

In certain embodiments, GIS may start the iteration from the most dependent layer, the output layer, and proceed towards to the least dependent layer, the hidden layer of the GOPmin. This may give the output layer to assign the best—so far—operator set at an initial stage so that a more convenient search can be made at the hidden layer accordingly. According to certain embodiments, when the GIS is accomplished for the output layer, the $\Theta^*_l$ found may still be the random operator (an operator randomly selected from $\Theta$) if the so-far best learning performance is achieved with that. Once the evaluation is completed for the output layer and the best operator set is found and assigned, the first GIS may then be carried out with the hidden layer and terminates afterwards. The second GIS may then be performed once again starting from the output layer again to see whether another operator set is now optimal with the recent assignment for the hidden layer. This may be possible because at the first GIS iteration, the optimal operator set for the first layer is found when the neurons at the output layer have initially random operator sets. When the second GIS terminates, one can be sure that the GOPmin now has just been trained by BP with the optimal operator sets assigned for both layers, hidden and output. If the best so far learning performance achieved is below the learning objective, then the formed hidden layer within GOPmin may be appended as the next hidden layer of the final POP, and the progressive formation of the next hidden layer of the POPmax may be performed in another GOPmin with the same two-pass GIS. Otherwise, the progressive formation of the final POP may now be terminated, and both hidden and output layers of the GOPmin may finally be appended to the final POP. This may be the case during the progressive formation of the GOPmin (3) in the sample illustration given in FIG. 4. The algorithm for the two-pass GIS over the operator library, $\Theta$, may be expressed in Table 4.

TABLE 4

Two-pass GIS in GOPmin(h)

Input: $\Theta$, POPmax, h
Output: GOPmin*(h, $\theta$)

Two-pass GIS Algorithm:

1) construct GOPmin(h) with the $h^{th}$ hidden and output layers of POPmax while all neurons having operator sets (nodal, pod and activation) randomly selected from $\Theta$
2) For l = 3 to 2, DO:
   a. For each operator set $\theta$, in $\Theta$ DO:
     i. Assign the operator set of each neuron in the $l^{th}$ layer of the GOPmin to $\theta \rightarrow$ GOPmin (h, $\theta_l$)
     ii. DO: Test-Run(GOPmin (h, $\theta_l$)) and RECORD: GOPmin *(h, $\theta$) that achieves the best performance
     iii. Assign $\theta_l^* = \theta_l$ if the best performance criterion is achieved with it during the operation of Test-Run(GOPmin (h, $\theta_l$))
   b. Assign the operator set of each neuron in the $l^{th}$ layer of the GOPmin (h, $\theta_l$) to $\theta_l^* \rightarrow$ GOPmin (h, $\theta_l^*$)
3) RETURN: GOPMin *(h, $\theta$) the best performing 3-layer GOP.

According to certain embodiments, during GIS passes, the best performing GOP with the optimal operator sets, GOPmin*(h, $\theta$), may be achieved at any iteration of any BP test-run, not necessarily at the end of the search process. This is because each assignment of the $\theta_l^*$ to the layer l neurons only guarantees that the operator set, $\theta^*_l$, is optimal providing that the operator set assigned to other layer is also optimal. If not, $\theta^*_l$ is just the best-so-far operator when other layer has those sub-optimal operator sets, which may suggest that $\theta^*_l$ is a local optimal solution. Therefore, the 3-layer GOP with the optimal operators, GOPmin*(h, $\theta$) may be the primary output of the GIS, not the one with the $\theta^*_l$ that is converged at the end of the two-pass GIS operation.

Table 5 presents a sample GIS operation over the 3-layer GOPmin(1) that is the GOPmin for the first hidden layer of the POPmax, according to certain embodiments. Initially, each GOP neuron may have an operator set randomly assigned from $\Theta$. As layer 0 is the input layer, initially the GOPmin may be represented as: I-R-R where 'I' represents the input layer without any operators, and 'R' represents random operator set assignment within $\Theta$ to that layer's neurons. In each layer the operator sets in $\Theta$ may now be present due to such random initialization, and a proper assessment may now be performed about the layerwise operator set assignments for the output layer. This is the $1^{st}$ GIS iteration, operator sets in $\Theta$, may be assigned to the output layer in a sequential order and evaluated by two consecutive test runs. The table presents the test run indices and the best performance achieved within (minimum MSE), according to certain embodiments, only if the test run with a particular operator set assignment achieves a better performance than the previous best result. Therefore, the last entry of each layer presents the minimum MSE from the best test-run, e.g., for GIS iteration 1 and layer2, minimum MSE=$0.416 \times 10^{-2}$ is achieved by the operator set 21 within $\Theta$ during the first test-run. This is why the operator set 21 is then assigned to the output layer and the search process continues for the layer 1 over the GOP: I-R-21. At the end of the 1st GIS iteration, the so-far best GOP has I-64-21 layout and, thus, the $2^{nd}$ GIS iteration now seeks for the best operator set for the output layer again while previous layer contains the $64^{th}$ operator set in $\Theta$ and, thus, verifies whether or not operator set21 is still the best for the output layer. For this sample problem it turns out that the operator set 31 in the output layer gives the best result.

TABLE 5

Starting with a 3-layer GOPmin with random operators (I-R-R) where I stands for the input layer and R stands for the random operator assignments for the hidden and the output layers, two GIS passes over the operator sets in $\Theta$ are illustrated by performing two test-runs per operator set.

| GIS Pass | Layer | Op. Set | Test-Run | MSE ($\times 10^{-2}$) | GOP Op. Sets |
|---|---|---|---|---|---|
| Init. | 1 + 2 | R | — | 19.43 | I-R-R |
| 1 | 2 | 21 | 1 | 0.416 | I-R-21 |
|  | 1 | 13 | 1 | 16.778 | I-13-21 |
|  |  | 19 | 2 | 12.553 | I-19-21 |
|  |  | 42 | 1 | 1.839 | I-42-21 |
|  |  | 54 | 2 | 0.258 | I-54-21 |
|  |  | 64 | 2 | 0.245 | I-64-21 |
| 2 | 2 | 18 | 1 | 0.24 | I-64-18 |
|  |  | 31 | 2 | 0.062 | I-64-31 |
|  | 1 | 11 | 1 | 19.195 | I-11-31 |
|  |  | 11 | 2 | 14.58 | I-11-31 |
|  |  | 31 | 1 | 0.131 | I-31-31 |
|  |  | 64 | 2 | 0.079 | I-60-31 |

As highlighted in Table 5, the best performance (minimum MSE=$6.2 \times 10^{-4}$) was achieved with the GOPmin*($\theta$), at the $2^{nd}$ GIS iteration during the $2^{nd}$ BP test-run while evaluating output layer with the operator set 31.

Experimental Results

In certain embodiments, there may be presented a large set of experiments conducted to evaluate learning performances and generalization potential of the POPs. For POPs, the sample nodal and pooling operators as given in Table 1 and Table 2 will be used along with the three activation operators: {tan h, linear, lincut} enumerated as {0, 1, 2}. For each operator, 0-enumeration is always used for the MLP operator (multiplication, summation and tan h). Therefore, a homogenous GOP with the operator set 0 having these default operators will be identical to the MLP. For the evaluation of the learning performance, a 6-layer POPmax was used with the configuration: In×48×24×12×6×Out, where In and Out are the input and output layer sizes that are determined by the learning problem. For fair comparative performance evaluations against MLPs and RBF networks, the same network configuration, learning parameters, and experimental setup will be used. In other words, when the final POP is formed, its network configuration and BP parameters will be used in the "equivalent MLP". However, since RBF networks can only have a single hidden layer, the equivalent RBF network may be formed having the number of hidden (Gaussian) neurons equivalent to the total number of all hidden neurons of the final POP. Moreover, deep (complex) MLP and RBF configurations may be used to see whether they are able to achieve a similar or better learning performance than the POPs.

Table 6 presents number of hidden neurons of all possible final POP configurations along with the deep and equivalent MLP and RBF networks, according to certain embodiments. For instance if the final POP is formed with the topology, In×48×24×Out, the equivalent MLP may be formed with the identical topology, and the equivalent RBF will have $\Sigma n=48+24=72$ Gaussian neurons. On the other hand, the deep MLP configuration may have 3 more hidden layers and 672 more hidden neurons for the same learning problem.

TABLE 6

Possible final POP, deep and equivalent MLP and RBF network configurations with their total number of hidden neurons ($\Sigma n$).

| Conf. | Network | Conf. | $\Sigma n$ |
|---|---|---|---|
| 1 | POP and Eq. MLP | In × 48 × Out | 48 |
| 2 | POP and Eq. MLP | In × 48 × 24 × Out | 72 |
| 3 | POP and Eq. MLP | In × 48 × 24 × 12 × Out | 84 |
| 4 | POP and Eq. MLP | In × 48 × 24 × 12 × 6 × Out | 90 |
| 5 | Deep MLP | In × 384 × 192 × 96 × 48 × 24 × Out | 744 |
| 6 | Eq. RBF | In × $\Sigma n$ × Out | $\Sigma n$ |
| 7 | Deep RBF | In × 744 × Out | 744 |

Since the dynamic range of all problems encountered is (or converted to) in the range of [−1, 1], the maximum output will correspond to 1 and all the others to −1. However, for those classification problems with a single output (e.g. all synthetic problems), a minimum 90% confidence level for each assignment (to 1 and −1) may be required, meaning that a classification error (CE) occurs if the actual output is not within the 10% range of the desired output.

TABLE 7

Operator enumeration (top) and the index of each operator set (bottom).

| | Op. Index: | | | | | |
|---|---|---|---|---|---|---|
| | 0 | 1 | 2 | 3 | 4 | 5 |
| Pool | sum | 1n-corr | 2n-corr | Max | | |
| Act. | tanh | linear | lincut | | | |
| Nodal | Mul. | Exp. | Sine | Quad. | Gauss. | DoG |

| | $\Theta$ Index | | |
|---|---|---|---|
| | Pool | Act. | Nodal |
| 0 | 0 | 0 | 0 |
| 1 | 0 | 0 | 1 |
| 2 | 0 | 0 | 2 |
| 3 | 0 | 0 | 3 |
| 4 | 0 | 0 | 4 |
| 5 | 0 | 0 | 5 |
| 6 | 0 | 1 | 0 |
| ... | ... | ... | ... |
| ... | ... | ... | ... |
| 65 | 3 | 1 | 5 |
| 66 | 3 | 2 | 0 |
| 67 | 3 | 2 | 1 |
| 68 | 3 | 2 | 2 |
| 69 | 3 | 2 | 3 |
| 70 | 3 | 2 | 4 |
| 71 | 3 | 2 | 5 |

The top section of Table 7 enumerates the operators in their corresponding sets, and the bottom section presents the index of each individual operator set in the operator library, $\Theta$, which may be used in the experiments, according to certain embodiments. There may be 4×3×6=72 operator sets in $\Theta$. During the progressive formation (PF) in each GOPmin, 2 BP test runs with maximum 500 epochs may be ran for the evaluation of each operator set in $\Theta$ for each layer of the GOPmin. Further, 10 PF operations may be performed to obtain the learning and generalization performance statistics, such as mean, standard deviation and the best performance score achieved. Afterwards, if the target learning objective is not achieved yet, as an optional post-process, the final POP with the best performance may further be trained by regular BP runs each with maximum 3000 epochs. For both BP test and regular runs, a global adaptation may be performed on the learning rate, i.e., for each BP iteration, t, with the MSE obtained at the output layer, E(t). A global adaptation of the learning rate, $\varepsilon$, is performed within the range $[5.10^{-1}, 5.10^{-5}]$, as follows:

$$E(t) = \begin{cases} \alpha\varepsilon(t-1) & \text{if } E(t) < E(t-1) \text{ and } \alpha\varepsilon(t-1) \leq 5.10^{-1} \\ \beta\varepsilon(t-1) & \text{if } E(t) \geq E(t-1) \text{ and } \beta\varepsilon(t-1) \geq 5.10^{-5} \\ \varepsilon(t-1) & \text{else} \end{cases} \quad (14)$$

where $\alpha=1.05$ and $\beta=0.7$, respectively. Each BP run may start with a random parameter initialization and store the network that achieves the best performance. For any BP run, a stopping criteria may be embedded, which may consist of the combination of maximum iteration number (e.g. 300 for test and 3000 for regular BP runs) and the target performance level, i.e., $10^{-4}$ for the MSE or $10^{-3}$ for the CE and 99% for F1 over the train dataset. When the target performance level is reached in any BP run (e.g. during a BP test run of a GIS) further BP runs may be omitted.

A. Evaluation of the Learning Performance

In order to evaluate the learning performance of the POPs, the most challenging synthetic problems may be used, such as Two-Spirals, N-bit parity problem, N-bit prime number estimation problem, 1-D and 2-D highly dynamic and multimodal function approximations, and uniform white noise approximation with 1000 samples. In order to test the learning scalability of the POPs, the dataset size of the three problems may be extended: Two-Spirals, N-bit Parity, and white noise approximation. Next each problem may be introduced briefly with their extensions.

1) Two-Spirals Problem

Figure 5:
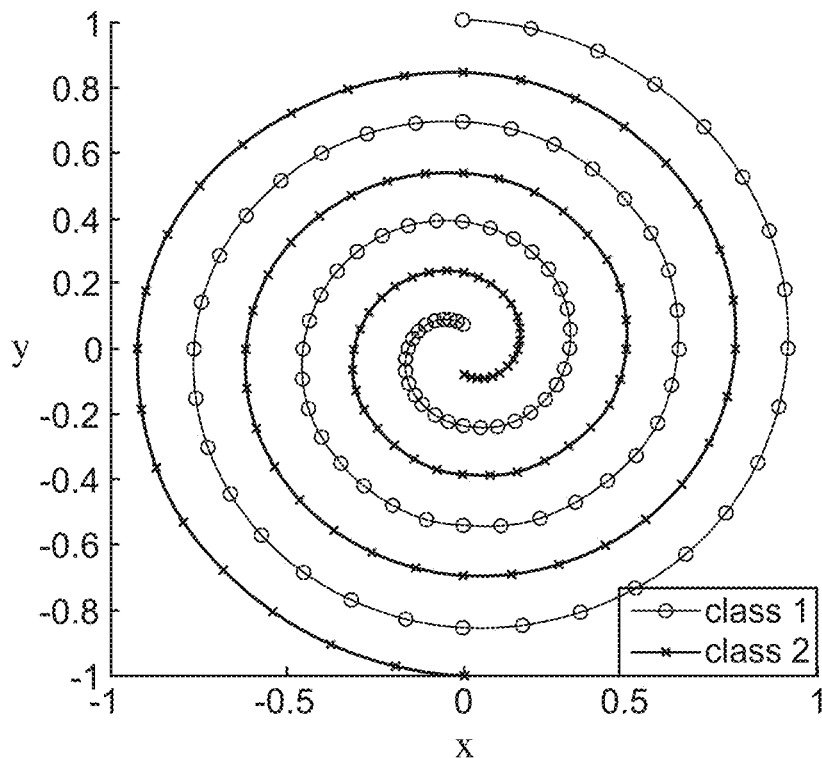
FIG. 5 illustrates a Two-Spirals problem, according to certain embodiments.

FIG. 5 illustrates a Two-Spirals problem, according to certain embodiments. In FIG. 5, the x-axis is labeled as "x", and the y-axis is labeled as "y", where the relationship between x and y is given by the underlying function, y=f(x). A Two-Spirals problem may be highly non-linear and possess further interesting properties. For instance, the 2D data may exhibit some temporal characteristics where radius and angle of the spiral vary with time. The error space may be highly multi-modal with many local minima. Thus, methods such as BP may encounter severe problems on error reduction. The data set may consist of 194 patterns (2D points), 97 samples in each of the two classes (spirals), and may be used as a benchmark for ANNs. Further, a near-optimum solution may not be obtained with standard BP algorithm over feed-forward ANNs. However, a special network structure with short-cut links between layers may be implemented. In certain cases, the problem may be unsolvable with 2-layers MLPs with 2×50×1 configuration. This therefore may be one of the hardest learning problems for conventional MLPs.

Figure 6:
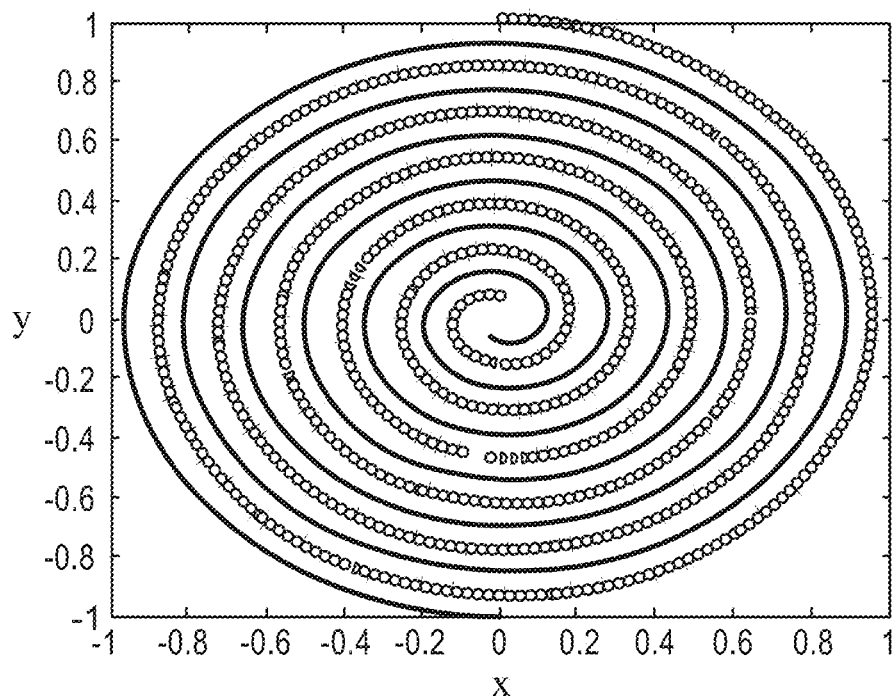
FIG. 6 illustrates an extended Two-Spirals of FIG. 5 with 30 times more data points than the original problem, according to certain embodiments.

FIG. 6 illustrates an extended Two-Spirals with 30 times more data points than the original problem, according to certain embodiments. In FIG. 6, the x-axis is labeled as "x", and the y-axis is labeled as "y", where the relationship between x and y is given by the underlying function, y=f(x). In view of the extension, there are now 30×194=5820 samples, and both spirals have also 3 times more densely rounding around each other.

2) 1-D and 2-D Function Approximations

Figure 7:
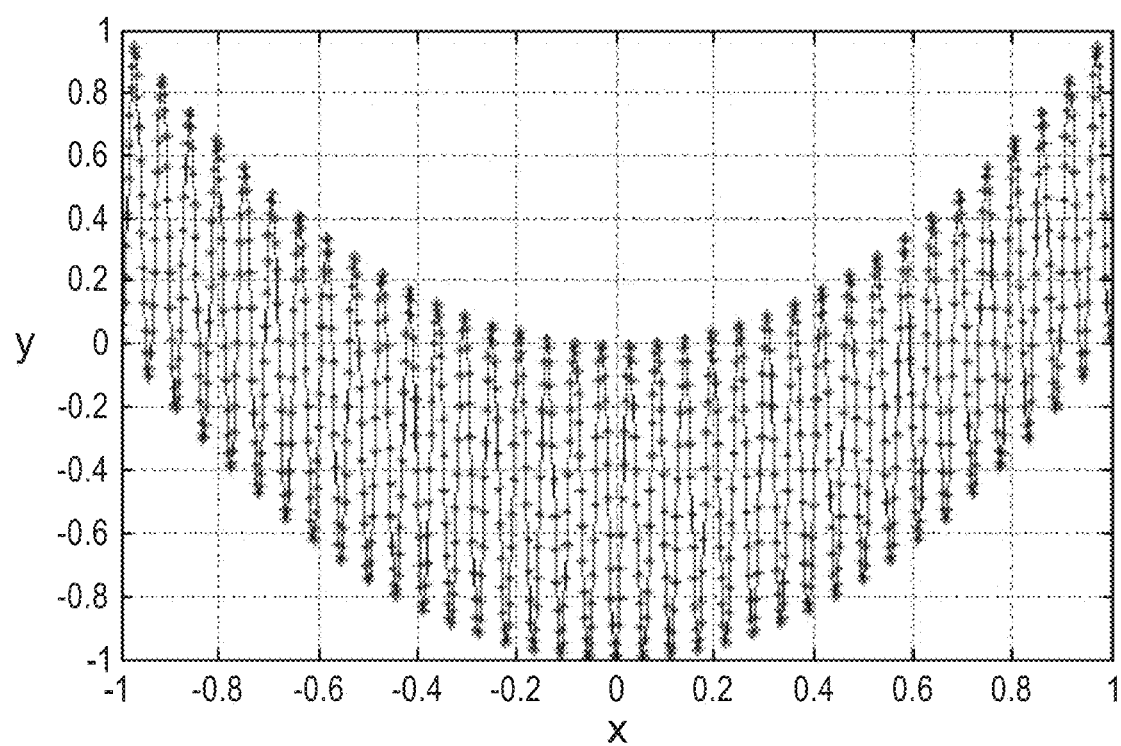
FIG. 7 illustrates a 1D Rastrigin function with 1,000 samples, according to certain embodiments.
Figure 8:
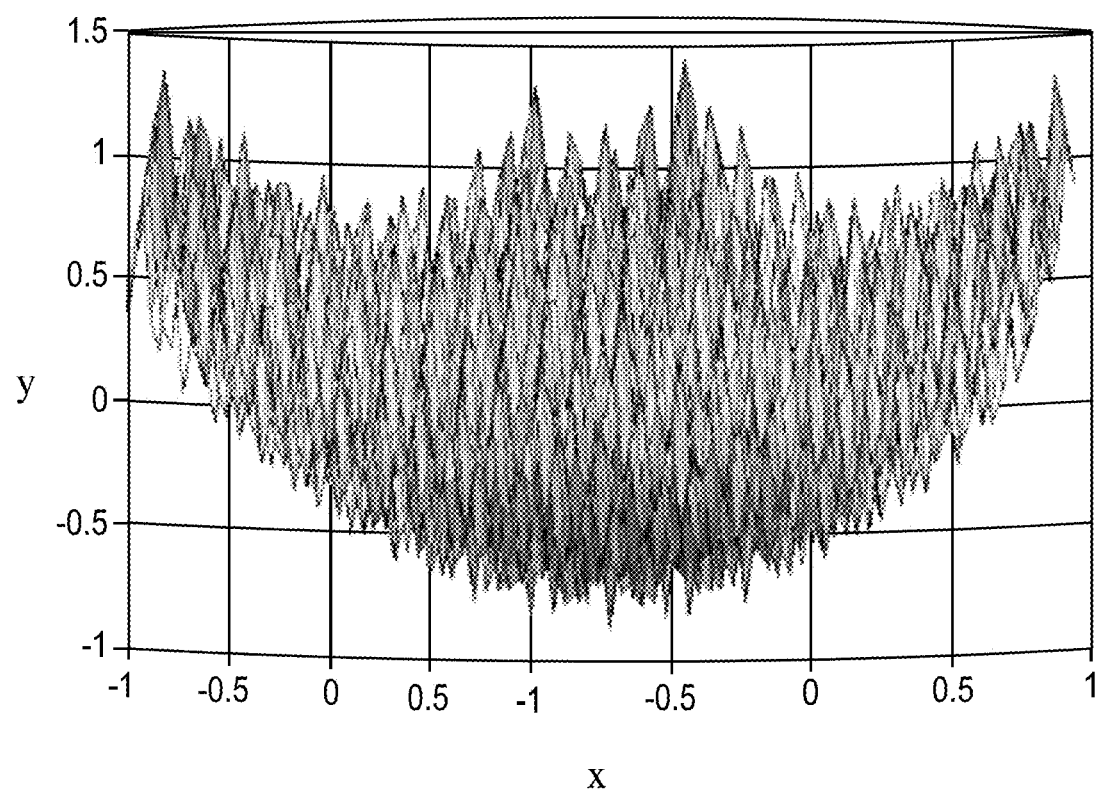
FIG. 8 illustrates a 2-D Rastrigin function with 2,500 samples according to certain embodiments.

FIG. 7 illustrates a 1D Rastrigin function with 1,000 samples, according to certain embodiments. Further, FIG. 8 illustrates a 2-D Rastrigin function with 2,500 samples, according to certain embodiments. In FIGS. 7 and 8, the x-axis is labeled as "x", and the y-axis is labeled as "y", where the relationship between x and y is given by the underlying function, y=f(x). Thus, as shown in FIG. 7 and FIG. 8, a highly dynamic and multimodal 1-D and 2-D Rastrigin functions were used for the function approximation, expressed in Eq. (15).

$$y=x^2-0.5(\cos(113x)-1) \text{ and}$$

$$z=K(x^2+y^2-0.5(\cos(113x)+\cos(113y)-1)) \quad (15)$$

where K=0.62 is the normalization coefficient to fit the function to [−1, 1] range. Further, the 1-D Rastrigin function has 1000 uniformly distributed points, and the 2-D function has a 50×50 grid of uniformly distributed 2500 points.

3) N-Bit Parity Problem

The N-bit parity problem may be defined in the following manner. Given a binary N-dimensional input vector, $x=(x_1, \ldots, x_N)$, the parity is 1 if the number of 1s is odd, otherwise 0. A 2-bit parity problem is identical to an XOR problem that cannot be solved by Single Layer Perceptrons (SLPs). Many studies on MLPs have been tested over the N-bit parity problem where N is kept low, e.g., 3<N<8. On such low N-bit parity problems, MLPs may provide solutions with varying accuracies. However as N gets bigger, MLPs, especially the simpler configurations with a single hidden layer, entirely fail to learn. Thus, in certain embodiments, N=12 was set, and comparative evaluations were performed with a dataset of $2^{12}$=4096 samples. The sample was then extended 8 times to $2^{15}$=32768 samples by setting N=15 in order to test the scalability performance of the POPs.

4) N-Bit Prime Number Problem

An N-bit prime number problem may be defined in the following manner. Given an input integer number, the objective is to learn whether the number is prime or not from its N-dimensional binary decomposition into an input vector, $x=(x1, \ldots, xN)$. The output is 1 if the number is prime, otherwise 0. In certain embodiments, N=12 was set, therefore, the prime numbers up to 4095 may be learned.

5) (Uniform) White Noise Approximation

Uniform white noise is a random signal with a uniform distribution, for example, ~U(−1, 1). The approximation of such a purely random signal may be a challenging learning problem since ideally there is no pattern for learning. However, the uniform random number generators in computers are actually not stochastic but a chaotic (pseudo-random) process which depends on a certain function that generates a sequence of numbers with respect to a seed number initially set. Furthermore, according to certain embodiments, the aim is to test POPs, whether or not they are capable of "approximating" some complex pattern over those pseudo-random numbers with the desired accuracy. For this purpose a white noise sequence is first generated with 1000 random numbers ~U(−1, 1) uniformly distributed in the range of [−1, 1]. The sequence is then extended to 5000 random numbers to test the scalability of the POPs. For this extension only, due to the severity of the problem, the number of hidden neurons of the POPmax was doubled.

Table 8 presents the learning performance statistics (mean, μ, standard deviation, σ, and the minimum) of the POPs and the conventional ANNs with the equivalent and deep configurations. The results are individually given for the 1-D and 2-D function approximation problem. Therefore, there are now results for 6 problems and 3 extensions. The corresponding final POP configuration can be seen from Table 6. Several important observations can be made. In the majority of the problems, the best POPs achieved 100% classification accuracy (CE=0) or MSE=0. Among the six problems encountered, for only two of them, the best result is achieved with a final POP that has the same number of hidden layers as the POPmax. This indicates a proper depth and hence a diversity adaptation according to the problem. This further reveals the crucial role of finding the right operator set for each layer to achieve such an elegant learning performance with the right depth. On the other hand none of the equivalent MLP or RBF configurations were able to achieve this and on the contrary, they entirely failed on the majority of the problems. Interestingly this is also true for deep MLP and RBF configurations even though the network size is increased more than 10 times with additional hidden layer(s). Although the learning performances somewhat improved, in general they still perform significantly worse than the POPs.

TABLE 8

The learning performances of the POPs and the conventional ANNs with equivalent and deep configurations over the six challenging learning problems and three of their extensions. POP configurations are listed in Table 6.

| No | Problems | Perf. Crit. | Best POP | Stats | POP | Eq. MLP | Eq. RBF | Deep MLP | Deep RBF |
|---|---|---|---|---|---|---|---|---|---|
| 1 | Two Spirals | CE | 3 | min. | 0 | 32.99 | 22.16 | 2.06 | 0 |
|   |   |   |   | $\mu \pm \sigma$ | 0 ± 0 | 49.90 ± 7.60 | 31.55 ± 6.22 | 36.70 ± 13.6 | 0 ± 0 |
| 2 | 1-D Rastrigin | MSE | 3 | min. | 0 | 12.47 | 1.25 | 0.93 | 0 |
|   |   |   |   | $\mu \pm \sigma$ | 0.29 ± 0.67 | 12.49 ± 0.02 | 3.69 ± 2.55 | 1.66 ± 0.52 | 2.32 ± 4.88 |
| 3 | 2-D Rastrigin | MSE | 4 | min. | 0.049 | 9.87 | 9.79 | 9.68 | 2.48 |
|   |   |   |   | $\mu \pm \sigma$ | 0.82 ± 0.39 | 9.90 ± 0.02 | 9.79 ± 0 | 9.78 ± 0.4 | 4.25 ± 1.45 |
| 4 | 12b Parity | CE | 1 | min. | 0 | 3.49 | 98.8 | 37.3 | 81.52 |
|   |   |   |   | $\mu \pm \sigma$ | 0 ± 0 | 15.13 ± 15.74 | 99.04 ± 0.50 | 48.91 ± 8.92 | 81.52 ± 0 |
| 5 | 12b Prime | CE | 1 | min. | 1.51 | 19.07 | 50 | 8.28 | 81.52 |
|   |   |   |   | $\mu \pm \sigma$ | 4.26 ± 0.73 | 21.12 ± 1.64 | 52.01 ± 2.93 | 11.64 ± 2.07 | 81.52 ± 0 |
| 6 | 1K White Noise | MSE | 4 | min. | 0 | 28.15 | 22.83 | 22.77 | 0.4 |
|   |   |   |   | $\mu \pm \sigma$ | 0 ± 0 | 28.87 ± 0.59 | 24.05 ± 1.06 | 23.03 ± 0.24 | 1.11 ± 0.92 |
| 7 | Ext. Two Spirals | CE | 2 | min. | 0 | 87.63 | 72.73 | 69.36 | 0 |
|   |   |   |   | $\mu \pm \sigma$ | 0.53 ± 0.94 | 90.37 ± 1.60 | 84.56 ± 11.3 | 74.61 ± 4.11 | 2.74 ± 7.70 |
| 8 | 5K White Noise | MSE | 4 | min. | 0.025 | 32.79 | 28.37 | 30.89 | 22.86 |
|   |   |   |   | $\mu \pm \sigma$ | 1.67 ± 2.58 | 32.88 ± 0.05 | 29.74 ± 0.89 | 31.15 ± 0.14 | 25.92 ± 1.93 |
| 9 | 15b Parity | CE | 1 | min. | 0 | 35.53 | NA | 0.4 | NA |
|   |   |   |   | $\mu \pm \sigma$ | 0 ± 0 | 68.53 ± 22.57 | NA | 46.92 ± 43.5 | NA |

Figure 9:
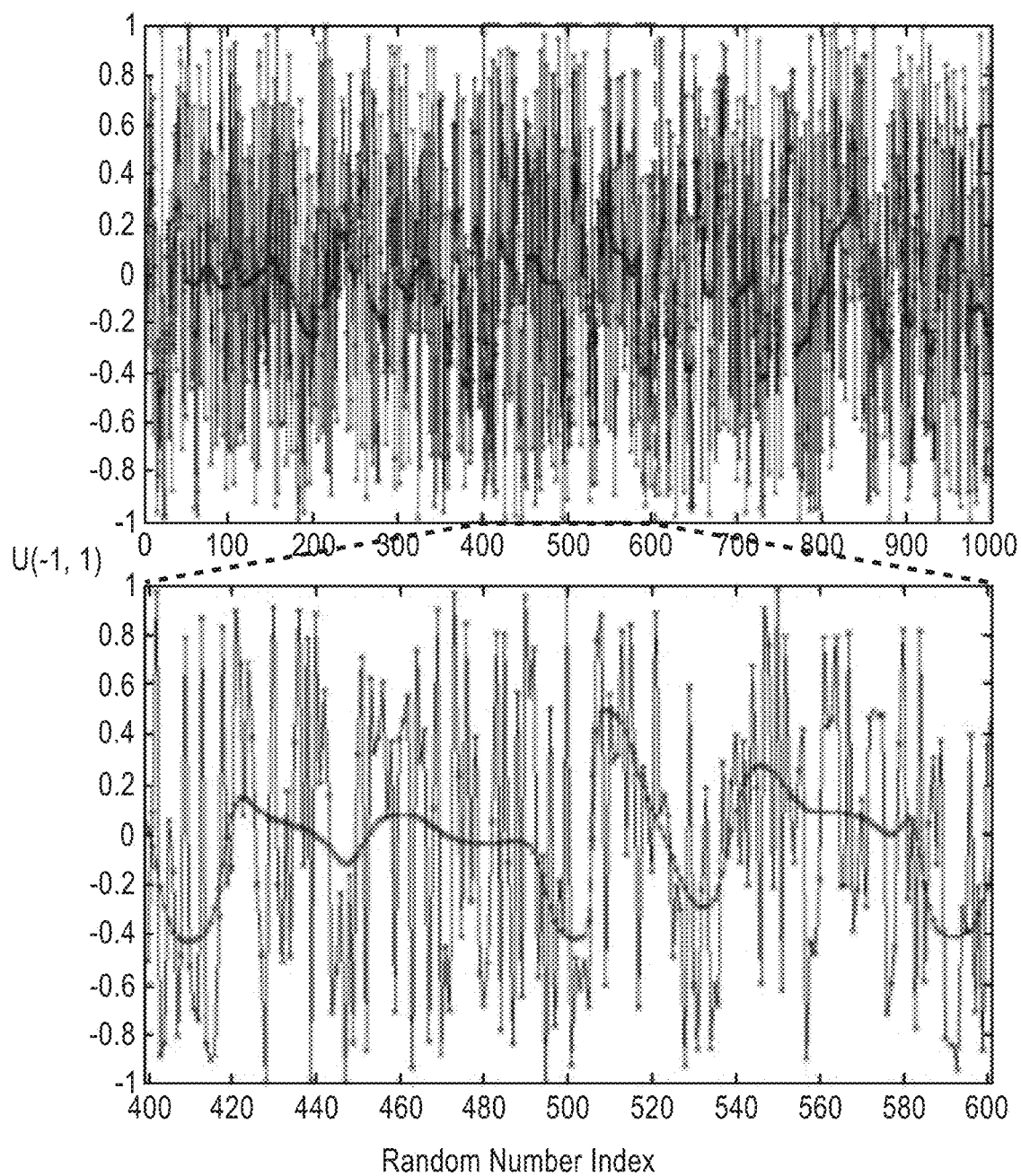
FIG. 9 (top) illustrates the 1,000 samples of white noise versus its approximation by the deep MLP with the best performance, and (bottom) the zoomed section, according to certain embodiments.

According to certain embodiments, the best performance achieved by the deep MLPs is: MSE=22.77×10$^{-2}$. A certain improvement is visible over the best result achieved by the equivalent MLPs (28.15×10$^{-2}$). FIG. 9 illustrates the top 1,000 samples of white noise versus its approximation by the deep MLP with the best performance, and (bottom) the zoomed section, according to certain embodiments. In FIG. 9, the x-axis is labeled as "random number index", and the y-axis is labeled as U(−1, 1). In particular, as shown in FIG. 9, this "improved" approximation is still a failure and hence the improvement is negligible. The best of the deep RBF networks, on the other hand, managed to achieve the learning objective for the two problems. This is an expected outcome since ANNs with only one arbitrarily large hidden layer could approximate a function to any level of precision. Further, deep RBFs have the hidden layer with 744 neurons and, therefore, over the two dataset with the least size, Two-Spirals (194) and 1-D Rastrigin (1,000), and even partially over the white noise (1,000) they achieved the target learning performance thanks to such a large hidden layer. This was however, no longer possible over the larger datasets with more than 2,000 samples. Of course, using such a sheer size of hidden neurons that is in the same scale with the dataset size may not be a feasible option for many real datasets.

From the initial results, neither configuration of conventional ANNs manage to learn any of the three extended problems. POPs, on the other hand, achieved a similar performance level as before and, thus, exhibit a high level of scalability. Further, with the same POPmax used for the two extended problems, the best POP achieved for 15bit Parity problem has a single hidden layer as for the 12 bit counterpart whereas it has only two hidden layers for the extended Two-Spirals problem as opposed to the three hidden layers for the original version. This indicates that as long as the right depth and operator sets are found, the POPs can still show the same performance level even though the dataset size is significantly increased (e.g., 30 times in this case). When the underlying pattern (or function) is properly modeled by the right blend of operators, the POPs performance should not be affected by the dataset size as long as the same pattern or function prevails.

Figure 10:
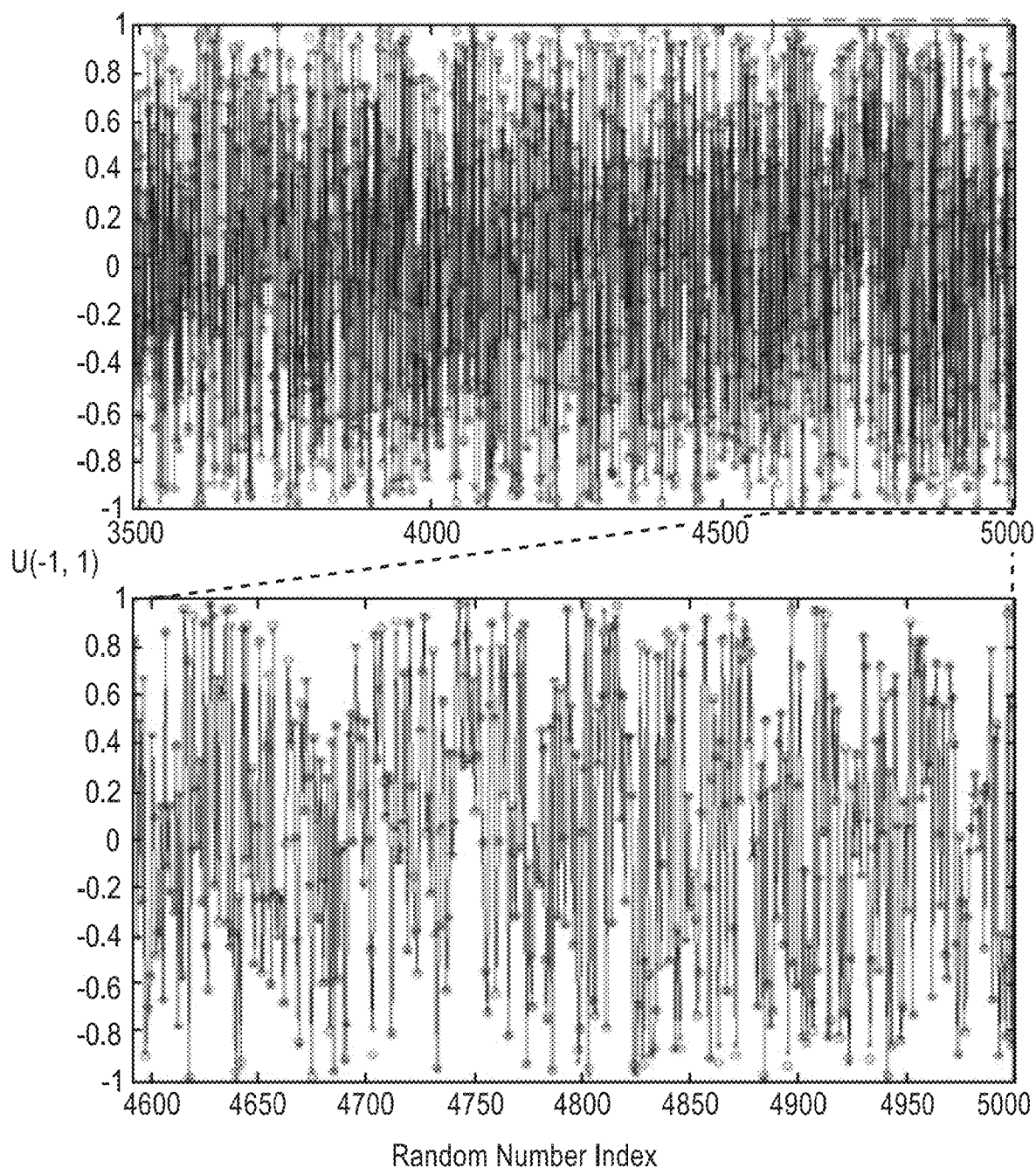
FIG. 10 (top) illustrates the last section of the 5,000 samples of white noise versus its approximation by the POP with the best performance and (bottom) the zoomed section, according to certain embodiments.

In the extreme case when there is no pattern or a function at all, as in the case of white noise signal, POPs may still cope with the problem as long as sufficient diversity is provided. This is indeed the case for the extended white noise approximation with 5,000 samples. The dataset size was increased 5 times, and it was demonstrated that it is sufficient to achieve a similar learning performance with a POPmax that has the same depth and only twice as many hidden neurons. FIG. 10 (top) illustrates the last section of the 5,000 samples of white noise versus its approximation by the POP with the best performance and (bottom) the zoomed section, according to certain embodiments. In FIG. 10, the x-axis is labeled as "random number index", and the y-axis is labeled as U(−1, 1). FIG. 10 also shows the approximation performance of the best POP over this dataset (MSE=2.5× 10$^{-4}$). For a reasonable visualization, only the data points within the range of [3,500, 5,000] are shown in FIG. 10.

B. Generalization Evaluations Over UCI Machine Learning (Proben1) Datasets

According to certain embodiments, the generalization capability of the GOPs over the real benchmark datasets having limited and scarce training data with missing attributes was evaluated. A reason behind this was to make the generalization a challenging task for a proper evaluation. Moreover, an even simpler POPmax configuration was used: In×24×12×6×Out. From the Proben1 repository, four benchmark classification problems were selected: breast cancer, heart disease, horse colic and diabetes, which are medical diagnosis problems with the following attributes: (a) All of them area real-world problems based on medical data from human patients; (b) The input and output attributes are similar to those used by a medical doctor; and (c) Since medical examples are expensive to obtain, the training sets were limited with occasional missing attributes.

1) Breast Cancer

The objective of this data set was to classify breast lumps as either benign or malignant according to microscopic examination of cells that are collected by needle aspiration. There are 699 exemplars of which 458 are benign and 241 are malignant, and they were originally partitioned as 350 for training, 175 for validation, and 174 for testing. The data set consists of 9 input and 2 output attributes, and was created at the University of Wisconsin Madison by Dr. William Wolberg.

2) Diabetes

This data set was used to predict diabetes diagnosis among Pima Indians. All patients reported were females of at least 21 years old. There were total of 768 exemplars of which 500 were classified as diabetes negative, and 268 as diabetes positive. The data set was originally partitioned as 384 for training, 192 for validation, and 192 for testing. It consists of 8 input and 2 output attributes.

3) Heart Disease

The initial data set consists of 920 exemplars with 35 input attributes, some of which were severely missing. Hence a second data set was composed using the cleanest part of the preceding set, which was created at Cleveland Clinic Foundation by Dr. Robert Detrano. The Cleveland data is called as "heartc" in the Proben1 repository and contains 303 exemplars, but 6 of them still contain missing data and hence discarded. The rest was partitioned as 149 for training, 74 for validation and 74 for testing. There were 13 input and 2 output attributes. The purpose was to predict the presence of the heart disease according to input attributes.

4) Horse Colic

This problem has many missing values (about 30% overall), and there were 364 records. The dataset was partitioned as 182 for training, 91 for validation and 91 for testing. There were 58 input and 3 output attributes. The purpose was to predict what happened to the horse and the outcomes are: 1—lived, 2—died and 3—euthanized.

According to certain embodiments, in order to evaluate the generalization capability of POPs, the best possible learning performance over the 'unseen' data—the test dataset was evaluated. For this purpose, only the best performance over the test set (i.e., the minimum test CE) was observed while training the conventional ANNs or forming the POPs. There were several methods to improve the generalization performance over the test datasets such as early stopping, parameter noising, drop-out, cross-validation, etc. However, these were beyond the scope of this work and hence not used herein. The objective was to evaluate the generalization potential of the POPs, for example, finding the best possible generalization capability achieved during each progressive formation or training run over the test data. Accordingly, comparative evaluations were performed against conventional ANNs under equal settings and conditions.

Table 9 presents the statistics of the best generalization performances observed during 10 training/progressive formation runs over the four Proben1 datasets, For the Cancer dataset, all ANNs easily achieved 100% classification accuracy on the test data since this is the simplest dataset with the most discriminative features. However, for the three other more challenging datasets, a significant generalization performance gap occurs between the POPs and the two other ANNs. The gap widens as the dataset becomes more challenging. For instance, the maximum gap occurs in the Horse dataset where 30% of the data is missing, which makes the learning the most difficult. This is an anticipated outcome due to the superior learning capability of the POPs that can model and learn complex, noisy or even missing patterns as demonstrated in the earlier experiments.

Figure 11:
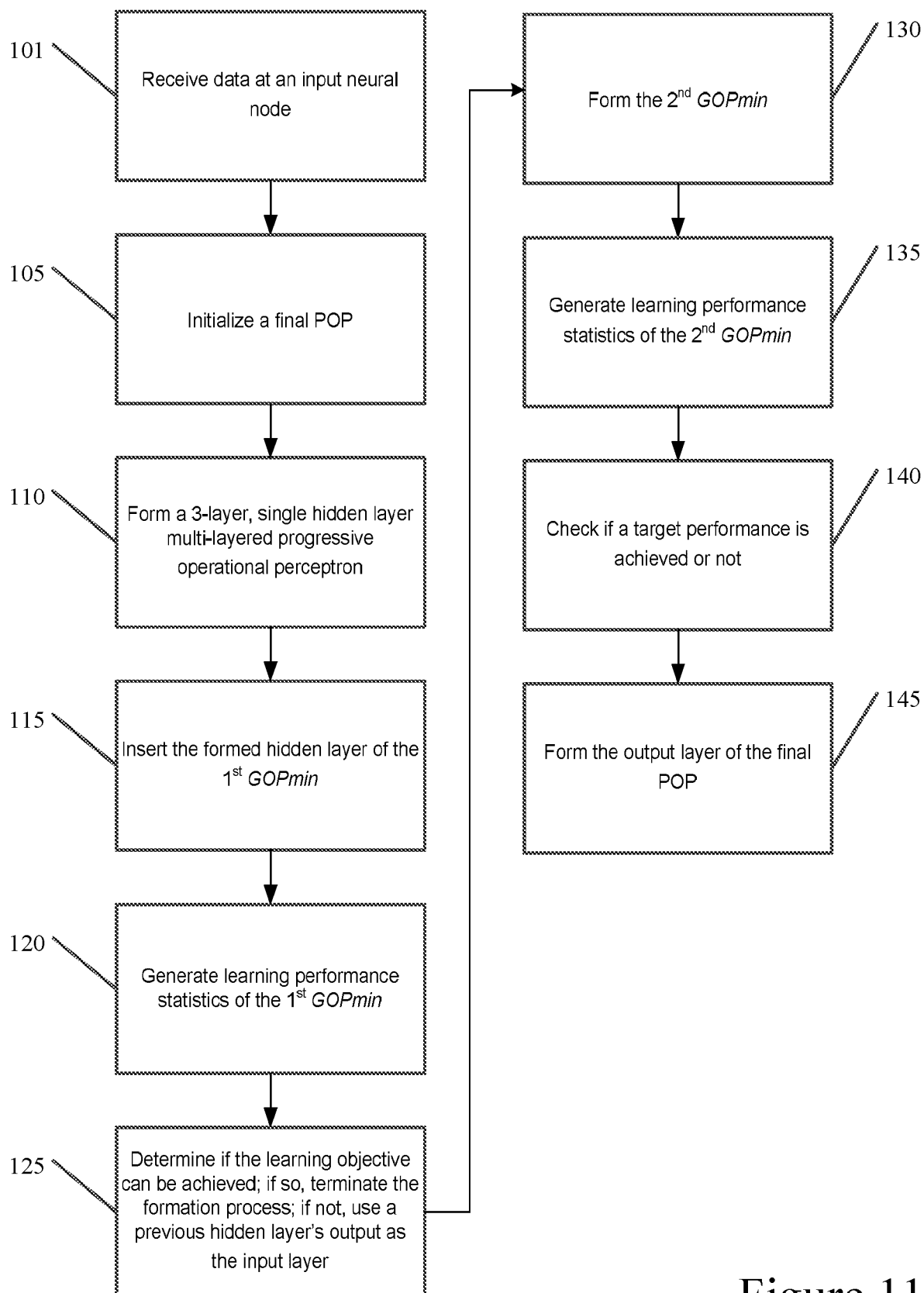
FIG. 11 illustrates a flow diagram, according to certain embodiments.

FIG. 11 illustrates a flow diagram according to certain embodiments. In particular, FIG. 11 illustrates a process that can be performed by a user device and/or a server described below. In step 101, data may be received at an input neural node of an input layer. In certain embodiments, the received data may correspond to a learning objective that is to be accomplished. In step 105, a final POP may be initialized by assigning the input layer as an input layer of a maximum POP configuration (POPmax). In step 110, a 3-layer, single hidden layer multi-layered progressive operational perceptron ($1^{st}$ GOPmin) may be created using the configurations of the input layer, a first hidden layer and an output layer of the POPmax. In step 115, the formed hidden layer of the $1^{st}$ GOPmin may be inserted as a first hidden layer of the final POP, and at step 120, learning performance statistics of the $1^{st}$ GOPmin may be generated.

Further, at step 125, it may be determined if the learning objective can be achieved with the $1^{st}$ GOPmin. If the learning objective can be achieved, the formation process is terminated. If the learning objective cannot be achieved, then the process may include using a previous hidden layer's output as the input layer by forward propagating training data, forming a second 3-layer, single hidden layer multi-layered progressive operational perceptron ($2^{nd}$ GOPmin) using the configurations of a second hidden layer of the POPmax as the hidden layer and the output layer of the, POPmax, as the output layer. At step 130, the $2^{nd}$ GOPmin may be formed and inserted as the $2^{nd}$ hidden layer of the final POP.

At step 135, learning performance statistics of the $2^{nd}$ GOPmin may be generated, and at step 140, it may be checked if a target performance is achieved with the $2^{nd}$ GOPmin. If not, the process may repeat the forming, checking, and inserting in the same order for a third, fourth, and additional GOPmin, until the target performance is achieved or all hidden layers of the POPmax are formed. At step 145, the output layer of the final POP may be formed as the output layer of the last GOPmin formed.

According to certain embodiments, the formation of the first hidden layer and additional hidden layers and the output layer may include determining optimal operators and parameters for neural nodes contained therein. In other embodiments, when it is determined that the learning objective can be achieved with the first hidden layer, the process may further include appending the first hidden layer to a final multi-layered progressive operation perceptron as its first hidden layer. According to certain embodiments, the formation of the first hidden layer and additional hidden layers may be carried out by a greedy iterative search. In other embodiments, the greedy iterative search may include performing a layerwise evaluation by sequentially assigning one operator set to all neural nodes of the first hidden layer and the additional hidden layers.

FIG. 12 illustrates a system according to certain embodiments. It should be understood that the contents of FIGS. 1-11 may be implemented by various means or their combinations, such as hardware, software, firmware, one or more processors and/or circuitry. In one embodiment, a system may include several devices, such as, for example, a user device 210 and/or a server 220. The system may include more than one user device 210 and more than one server 220.

The user device 210 and server 220 may each include at least one processor 211 and 221. At least one memory may be provided in each device, and indicated as 212 and 222, respectively. The memory may include computer program instructions or computer code contained therein. One or more transceivers 213 and 223 may be provided, and each device may also include an antenna, an antenna respectively illustrated as 214 and 224. Although only one antenna each is shown, many antennas and multiple antenna elements may be provided to each of the devices. Other configurations of these devices, for example, may be provided. For example, user device 210 and server 220 may be additionally configured for wired communication, in addition to wireless communication, and in such a case antennas 214 and 224 may illustrate any form of communication hardware, without being limited to merely an antenna.

Transceivers 213 and 223 may each, independently, be a transmitter, a receiver, or both a transmitter and a receiver, or a unit or device that may be configured both for transmission and reception. Further, one or more functionalities may also be implemented as virtual application(s) in software that can run on a server.

User device 210 may be a mobile station (MS) such as a mobile phone or smart phone or multimedia device, a computer, such as a tablet, laptop computer or desktop computer, provided with wireless communication capabilities, personal data or digital assistant (PDA) provided with wireless communication capabilities. However, certain embodiments may be implemented wherever any ANN can be implemented, which may further include on a cloud computing platform or a server.

In some embodiments, an apparatus, such as the user device 210 or server 220, may include means for carrying out embodiments described above in relation to FIGS. 1-11. In certain embodiments, at least one memory including computer program code can be configured to, with the at least one processor, cause the apparatus at least to perform any of the processes described herein.

Processors 211 and 221 may be embodied by any computational or data processing device, such as a central processing unit (CPU), digital signal processor (DSP), application specific integrated circuit (ASIC), programmable logic device (PLDs), field programmable gate arrays (FPGAs), digitally enhanced circuits, or comparable device or a combination thereof. The processors may be implemented as a single controller, or a plurality of controllers or processors.

For firmware or software, the implementation may include modules or unit of at least one chip set (for example, procedures, functions, and so on). Memories 212 and 222 may independently be any suitable storage device such as those described above. The memory and the computer program instructions may be configured, with the processor for the particular device, to cause a hardware apparatus such as user device 210 or server 220, to perform any of the processes described above (see, for example, FIGS. 1-11). Therefore, in certain embodiments, a non-transitory computer-readable medium may be encoded with computer instructions or one or more computer program (such as added or updated software routine, applet or macro) that, when executed in hardware, may perform a process such as one of the processes described herein. Alternatively, certain embodiments may be performed entirely in hardware.

Certain embodiments tackled the well-known problems and limitations of the feed-forward ANNs with a generalized model of the biological neurons. The GOP model of certain embodiments allows the encapsulation of many linear and non-linear operators in order to achieve an elegant diversity, and a better model of the synaptic connections, along with the integration process at the soma of the biological neuron cells. Even though the BP method was modified to train any GOP, only the right operator set with the properly trained parameters can truly provide the right blend of kernel transformations to accurately approximate or to model the underlying complex function/surface of the learning problem. This issue has been addressed by proposing POPs that are self-organized and depth-adaptive.

In the progressive formation approach, according to certain embodiments, it may be possible for the optimal operator set for each hidden layer to be searched iteratively, and their parameters may be optimized simultaneously by the modified BP. Such a layer-wise formation avoids redundant hidden layer formations and creates the final POP with the right depth and diversity required by the learning problem complexity. An extensive set of experiments, according to certain embodiments, show that POPs can provide a tremendous diversity and hence can manage the most challenging learning problems that cannot be learned even partially by conventional ANNs with deeper and significantly complex configurations. In particular, in the white noise approximation problem there is no pattern for learning. However, the final POP with the proper depth was able to fit a complex function even over such random data with the desired accuracy. Furthermore, it was observed that when the data size is significantly increased, POPs can scale up well as long as the major data patterns prevail.

Although the foregoing description is directed to the preferred embodiments of the invention, it is noted that other variation and modifications will be apparent to those skilled in the art, and may be made without departing from the spirit or scope of the invention. Moreover, features described in connection with one embodiment of the invention may be used in conjunction with other embodiments, even if not explicitly stated above.

Furthermore, the results over the four benchmark Proben1 datasets show that the best generalization performance that the POPs can achieve may be equivalent or better than what conventional ANNs can. It is noted that these results still promise a baseline learning performance, whereas the gap can further be widened when the operator library is enriched especially with such nodal and pool operators that can further boost the diversity.

According to certain embodiments therefore, it may be possible to address the various limitations and drawbacks of the traditional neuron model of MLPs by a generalized model of the biological neurons with the use of non-linear operators. It may also be possible to provide GOPs that are built in a progressive way similar to the biological neural networks. In addition, POPs may share the same properties of classical MLPs including but not limited to, for example, at least feed-forward, fully-connected, layered, biased, trainable by back-propagation, etc., and can be identical to an MLP providing that the native MLP operators are used. Thus, in certain embodiments, POPs cannot perform worse than MLPs.

According to other embodiments, it may further be possible to provide the best set of operators to be searched. In addition, with the right blend of non-linear operators, POPs may learn very complex problems that cannot be learned by deeper and more complex MLPs. In other embodiments, GOPs and POPs may conveniently be used in any application where any other classifier (e.g., ANNs, SVMs, RF, etc.) is used.

Although the foregoing description is directed to the preferred embodiments of the invention, it is noted that other variation and modifications will be apparent to those skilled in the art, and may be made without departing from the spirit or scope of the invention. Moreover, features described in connection with one embodiment of the invention may be used in conjunction with other embodiments, even if not explicitly stated above.

We claim:

1. A method, comprising:
receiving data at an input neural node of an input layer, the received data corresponding to a learning objective that is to be accomplished;
generating a final progressive operational perceptron (final POP) by assigning the input layer as an input layer of a maximum POP configuration (POPmax), wherein the POPmax is defined as a maximum depth POP topology with h max hidden layers, and wherein the final POP is defined as corresponding to a final depth less than or equal to the POPmax;
forming a 3-hidden layer POP from a 4-hidden layer POPmax using a configuration of the input layer, a first hidden layer and an output layer of the POPmax;
inserting a formed hidden layer of first minimal depth generalized operational perceptron (GOPmin(1)) at a first training iteration as a first hidden layer of the final POP;
generating learning performance statistics of the GOPmin (1);
determining if the learning objective can be achieved with the GOPmin(1);
if the learning objective is achieved, terminate the formation process;
if the learning objective cannot be achieved with the GOPmin(1), using a previous hidden layer's output as the input layer by forward propagating training data, forming a second minimal depth generalization operational perception (GOPmin(2)) at a second training iteration using the configurations of a second hidden layer of the POPmax as the hidden layer and the output layer of the, POPmax, as the output layer;
forming the GOPmin(2) and inserting the formed hidden layer of the GOPmin(2) as a $2^{nd}$ hidden layer of the final POP;
generating learning performance statistics of the GOPmin (2);
checking if a target performance is achieved or not with the GOPmin(2), and if not achieved, repeat: forming, checking and inserting in the same order for a third, fourth, and additional GOPmin, until the target performance is achieved or all hidden layers of POPmax are formed; and
forming the output layer of the final POP as the output layer of the last GOPmin formed.

2. The method according to claim 1, wherein the formation of the first hidden layer and additional hidden layers and the output layer comprises determining optimal operators and parameters for neural nodes contained therein.

3. The method according to claim 1, wherein when it is determined that the learning objective can be achieved with the first hidden layer, the method further comprises appending the first hidden layer to a final multi-layered progressive operation perceptron as its first hidden layer.

4. The method according to claim 1, wherein the formation of the first hidden layer and additional hidden layers is carried out by a greedy iterative search.

5. The method according to claim 4, wherein the greedy iterative search comprises performing a layerwise evaluation by sequentially assigning one operator set to all neural nodes of the first hidden layer and the additional hidden layers.

6. An apparatus, comprising:
at least one memory comprising computer program code; and
at least one processor;
wherein the at least one memory and the computer program code are configured, with the at least one processor, to cause the apparatus at least to:
receive data at an input neural node of an input layer, the received data corresponding to a learning objective that is to be accomplished;
form a 3-hidden layer progressive operational perceptron (POP) from a 4-hidden layer maximum POP configuration (POPmax) using a first hidden layer of a first minimal depth generalized operation perception (GOPmin(1)) at a first training iteration and an output layer of the POPmax;
determine if the learning objective can be achieved with the GOPmin(1);
if the learning objective cannot be achieved with the first hidden layer, use a previous hidden layer's output as the input layer, forming a second minimal depth generalization operational perception (GOPmin(2) using a second hidden layer as the only hidden layer and the output layer of the POPmax;
train the GOPmin(2) and check if a target performance is achieved or not, and if not achieved, repeat the training and checking until the target performance is achieved or all hidden layers of POPmax are formed;
form an output layer corresponding to the first hidden layer and any additional hidden layers; and
generate learning performance statistics based on the received data.

7. The apparatus according to claim 6, wherein the formation of the first hidden layer and the additional hidden layers comprises determining optimal operators and parameters for neural nodes contained therein.

8. The apparatus according to claim 6, wherein when it is determined that the learning objective can be achieved with the first hidden layer, the at least one memory and the computer program code are further configured, with the at least one processor, to cause the apparatus at least to append the first hidden layer to a final layer of the multi-layered progressive operation perceptron.

9. The apparatus according to claim 6, wherein the formation of the first hidden layer and the additional hidden layers is carried out by a greedy iterative search.

10. The apparatus according to claim 9, wherein the greedy iterative search comprises performing a layerwise evaluation by sequentially assigning one operator set to all neural nodes of the first hidden layer and the additional hidden layers.

11. A computer program, embodied on a non-transitory computer readable medium, the computer program, when executed by a processor, causes the processor to:
receive data at an input neural node of an input layer, the received data corresponding to a learning objective that is to be accomplished;
form a 3-hidden layer progressive operational perceptron (POP) from a 4-hidden layer maximum POP configuration (POPmax) using a first hidden layer of a first minimal depth generalized operation perception (GOPmin(1)) at a first training iteration and an output layer of the POPmax;
determine if the learning objective can be achieved with the GOPmin(1);
if the learning objective cannot be achieved with the first hidden layer, use a previous hidden layer's output as the input layer, forming a second minimal depth generalization operational perception (GOPmin(2)) using a second hidden layer as the only hidden layer and the output layer of the POPmax;

train the GOPmin(2) and check if a target performance is achieved or not, and if not achieved, repeat the training and checking until the target performance is achieved or all hidden layers of POPmax are formed;

form an output layer corresponding to the first hidden layer and any additional hidden layers; and generate learning performance statistics based on the received data.

12. The computer program according to claim 11, wherein the formation of the first hidden layer and the additional hidden layers comprises determining optimal operators and parameters for neural nodes contained therein.

13. The computer program according to claim 11, wherein when it is determined that the learning objective can be achieved with the first hidden layer, the computer program, when executed by a processor, further causes the processor to append the first hidden layer to a final layer of the multi-layered progressive operation perceptron.

14. The computer program according to claim 11, wherein the formation of the first hidden layer and the additional hidden layers is carried out by a greedy iterative search.

15. The computer program according to claim 14, wherein the greedy iterative search comprises performing a layerwise evaluation by sequentially assigning one operator set to all neural nodes of the first hidden layer and the additional hidden layers.

* * * * *